(12) United States Patent
Murphy et al.

(10) Patent No.: US 7,807,370 B2
(45) Date of Patent: Oct. 5, 2010

(54) METHODS FOR IDENTIFICATION OF MERLE GENE

(75) Inventors: Keith E. Murphy, College Station, TX (US); Leigh Anne Clark, College Station, TX (US); Jacquelyn Wahl, Snook, TX (US); Christine Rees, Magnolia, TX (US)

(73) Assignee: Merlogen, LLC, Clemson, SC (US)

( * ) Notice: Subject to any disclaimer, the term of this patent is extended or adjusted under 35 U.S.C. 154(b) by 21 days.

(21) Appl. No.: 12/063,964

(22) PCT Filed: Aug. 16, 2006

(86) PCT No.: PCT/US2006/032100

§ 371 (c)(1),
(2), (4) Date: Feb. 15, 2008

(87) PCT Pub. No.: WO2007/022335

PCT Pub. Date: Feb. 22, 2007

(65) Prior Publication Data

US 2008/0227102 A1    Sep. 18, 2008

Related U.S. Application Data

(60) Provisional application No. 60/708,589, filed on Aug. 16, 2005.

(51) Int. Cl.
*C12Q 1/68*    (2006.01)
*C12P 19/34*    (2006.01)
*C07H 21/04*    (2006.01)

(52) U.S. Cl. .................. 435/6; 435/91.2; 536/23.1; 536/24.31; 536/24.33

(58) Field of Classification Search .................. None
See application file for complete search history.

(56) References Cited

U.S. PATENT DOCUMENTS

| | | | |
|---|---|---|---|
| 4,582,788 | A | 4/1986 | Erlich |
| 4,656,127 | A | 4/1987 | Mundy et al. |
| 4,683,194 | A | 7/1987 | Saiki et al. |
| 4,683,202 | A | 7/1987 | Mullis et al. |
| 4,988,617 | A | 1/1991 | Landegren et al. |
| 5,143,854 | A | 9/1992 | Pirrung et al. |
| 5,202,231 | A | 4/1993 | Drmanac et al. |
| 5,324,633 | A | 6/1994 | Fodor et al. |
| 5,405,783 | A | 4/1995 | Pirrung et al. |
| 5,424,186 | A | 6/1995 | Fodor et al. |
| 5,552,270 | A | 9/1996 | Khrapko et al. |
| 2003/0211486 | A1 | 11/2003 | Frudakis |
| 2006/0183127 | A1 | 8/2006 | Oulmouden et al. |

FOREIGN PATENT DOCUMENTS

| | | |
|---|---|---|
| EP | 0 050 424 | 4/1982 |
| EP | 0 084 796 | 8/1983 |
| EP | 0 201 184 | 11/1986 |
| EP | 0 237 362 | 9/1987 |
| EP | 0 258 017 | 3/1988 |
| FR | 2 650 840 | 2/1991 |
| FR | 2 857 979 | 1/2005 |
| WO | WO 89/10977 | 11/1989 |
| WO | WO 90/15070 | 12/1990 |
| WO | WO 91/02087 | 2/1991 |
| WO | WO 91/17239 | 11/1991 |
| WO | WO 92/10588 | 6/1992 |
| WO | WO 92/15712 | 9/1992 |
| WO | WO 92/16655 | 10/1992 |
| WO | WO 93/17126 | 9/1993 |
| WO | WO 94/11530 | 5/1994 |

OTHER PUBLICATIONS

GenBank GI:189789 [online] Apr. 28, 1996 [retrieved on Nov. 6, 2009] retrieved from http://www.ncbi.nlm.nih.gov/nuccore/189789.*
GenBank GI:1125061 [online] Aug. 7, 2000 [retrieved on Nov. 6, 2009] retrieved from http://www.ncbi.nlm.nih.gov/nuccore/1125061.*
GenBank GI:67966276 [online] Jun. 18, 2005 [retrieved on Nov. 6, 2009] retrieved from http://www.ncbi.nlm.nih.gov/sviewer/viewer.fcgi?67966276:OLD04:3557506.*
Abdelhak, et al., "Clustering of mutations responsible for branchio-oto-renal (BOR) syndrome in the eyes absent homologous region (eyaHR) of EYA1", *Hum. Mol. Genet.*, 6(13):2247-55 (1997).
Bailin, et al. "Genomic organization and sequence of D12S53E (Pmel 17), the human homologue of the mouse silver (si) locus", *J. Invest. Dermatol.*, 106(1):24-7 (1996).
Baldwin, "An exonic mutation in the HuP2 paired domain gene causes Waardenburg's syndrome", *Nature*, 355(6361):637-638 (1992).
Baxter and Pavan, "Pmel17 expression is Mitf-dependent and reveals cranial melanoblast migration during murine development", *Gene Expr. Patterns*, 3(6):703-7 (2003).
Choi, et al., "Three cases of Waardenburg syndrome type 2 in a Korean family", *Korean J. Ophthalmol.*, 18(2):185-189 (2004).
Clark, et al., "Chromosome-specific microsatellite multiplex sets for linkage studies in the domestic dog", *Genomics*, 84(3):550-4 (2004).
Clark, et al., "Retrotransposon insertion in SILV is responsible for merle patterning of the domestic dog", *Proc. Natl. Acad. Sci., USA*, 103(5):1376-81 (2006).
Cordaux and Batzer, "Teaching an old dog new tricks: SINEs of canine genomic diversity", *Proc. Natl. Acad. Sci. USA*, 103(5):1157-8 (2006).
Dausch, et al., "Ophthalmological findings in Merle dachshunds", *Dtsch. Tierarztl. Wochenschr.*, 84(12):468-75 (1977) (w/ English Abstract).

(Continued)

*Primary Examiner*—Samuel Woolwine
(74) *Attorney, Agent, or Firm*—Pabst Patent Group LLP

(57) ABSTRACT

Animals with mutations in SILV present with the merle coat color pattern phenotype. Methods for the identification of animals that harbor a mutation in the SILV gene are described. Mutations in the SILV gene can be identified from any biological sample such as a cell or tissue that contains genomic DNA. A microsatellite marker identified using linkage disequilibrium mapping that segregates with merle is also described.

11 Claims, 4 Drawing Sheets

OTHER PUBLICATIONS

Du, et al., "MLANA/MART1 and SILV/PMEL17/GP100 are transcriptionally regulated by MITF in melanocytes and melanoma", *Am. J. Pathol.*, 163(1):333-43 (2003).

*EMBL Nucleotide Sequence Database*, "Accession No. C01052", Jul. 17, 1996.

*EMBL Nucleotide Sequence Database*, "Accession No. CE177786", Sep. 29, 2003.

Fletcher, et al., "Evaluation of a short interspersed nucleotide element in the 3' untranslated region of the defective dystrophin gene of dogs with muscular dystrophy", *Am. J. Vet. Res.*, 62(12):1964-8 (2001).

Gelatt & McGill, "Clinical characteristics of microphthalmia with colobomas of the Australian Shepherd Dog", *J. Am. Vet. Med. Assoc.*, 162(5):393-396 (1973).

Guyon, et al., "A 1-Mb resolution radiation hybrid map of the canine genome", *Proc. Natl. Acad. Sci. USA*, 100(9):5296-301 (2003).

Hedan, et al., "Coat colour in dogs: identification of the merle locus in the Australian shepherd breed", *BMC Vet. Res.*, 27;2:9 (2006).

Jeoung, et al. "A SINE element in the canine D2 dopamine receptor gene and its chromosomal location", *Anim. Genet.*, 31(5):334-5 (2000).

Kerje, et al., "The Dominant white, Dun and Smoky color variants in chicken are associated with insertion/deletion polymorphisms in the PMEL17 gene", *Genetics*, 168(3):1507-18 (2004).

Kirkness, et al., "The dog genome: survey sequencing and comparative analysis", *Science*, 301(5641):1898-903 (2003).

Klinchmann, et al. "Light microscopy studies of the cornea of Merle dachshunds", *Dtsch. Tierarztl. Wochenschr.*, 94(6):338-41 (1987) (w/ English Abstract).

Klinckmann and Wegner, "Tonometry in Merle dogs", *Dtsch. Tierarztl. Wochenschr.*, 94(6):337-8 (1987) (w/ English Abstract).

Kushimoto, et al., "A model for melanosome biogenesis based on the purification and analysis of early melanosomes", *Proc. Natl. Acad. Sci. USA*, 98(19):10698-703 (2001).

Kwon, et al., "A melanocyte-specific gene, Pmel 17, maps near the silver coat color locus on mouse chromosome 10 and is in a syntenic region on human chromosome 12", *Proc. Natl. Acad Sci. USA*, 88(20):9228-9232 (1991).

Kwon, et al., "Mouse silver mutation is caused by a single base insertion in the putative cytoplasmic domain of Pmel 17", *Nucleic Acids Research*, 23(1):154-158 (1995).

Lin, et al., "The sleep disorder canine narcolepsy is caused by a mutation in the hypocretin (orexin) receptor 2 gene", *Cell*, 98(3):365-76 (1999).

McCallion and Chakravarti, "EDNRB/EDN3 and Hirschsprung disease type II", *Pigment Cell Res.*, 14(3):161-169 (2001).

Minnick, et al., "A highly repetitive DNA sequence possibly unique to canids", *Gene*, 110(2), 235-238 (1992).

Mitchell, "Dominant dilution and other color factors in collie dogs", *J. Hered.*, 26:425-430 (1935).

Nayak and Isaacson, "Worldwide distribution of Waardenburg syndrome", *Ann. Otol. Rhinol. Laryngol.*, 112(9 Pt 1):817-20 (2003).

Neff, et al., "Breed distribution and history of canine mdr1-1Delta, a pharmacogenetic mutation that marks the emergence of breeds from the collie lineage", *Proc. Natl. Acad. Sci. USA*, 101:11725-11730 (2004).

Nichols, et al., "A novel splice variant of Pmel17 expressed by human melanocytes and melanoma cells lacking some of the internal repeats", *J. Invest. Dermatol.*, 121(4):821-30 (2003).

O'Sullivan & Robinson, "Harlequin colour in the Great Dane dog", *Genetica*, 78(3):215-8 (1988-1989).

Pele, et al., "Harlequin colour in the Great Dane dog", *Hum. Mol. Genet.*, 14, 1417-1427 (2005).

Philipp, et al., "Polymorphisms within the canine MLPH gene are associated with dilute coat color in dogs", *BMC Genet.*, 6:34 (2005).

Pingault, et al., "SOX10 mutations in patients with Waardenburg-Hirschsprung disease", *Nat. Genet.*, 18(2):171-173 (1998).

Probe, et al., "A system for rapid DNA sequencing with fluorescent chain-terminating dideoxynucleotides", *Science*, 238:336-341 (1987).

Puffenberger, et al., "A missense mutation of the endothelin-B receptor gene in multigenic Hirschsprung's disease", *Cell*, 79(7):1257-1266 (1994).

Ray, et al., "A highly polymorphic RFLP marker in the canine transducin alpha-1 subunit gene", *Animal Genetics*, 27:372-373 (1996).

Ray, et al., "Molecular diagnostic test for ascertainment of genotype at the rod cone dysplasia (RCD1) locus in Irish Setters", *Current Eye Research*, 14:243-247 (1995).

Ray, et al., "PCR/RFLP marker in the canine opsin gene", *Animal Genetics*, 27:293-294 (1996).

Reetz, et al., "Audiometric findings in dachshunds (merle gene carriers)", *Dtsch. Tierarztl. Wochenschr.*, 84(7):273-7 (1977) (w/ English Abstract).

Schaible & Brumbaugh, "Electron microscopy of Pigmented Cells inVariegated and nonvariegated, Piebald-Spotted dogs", *Pigment Cell*, 3:191-200 (1976).

Schmutz, et al, "KITLG maps to canine chromosome 15 and is excluded as a candidate gene for merle in dogs", *Anim. Genet*, 34(1):75-6 (2003).

Shedlock, et al., "SINEs of speciation: tracking lineages with retroposons", *Trends in Eco. Evol.*, 19:545-553 (2004).

Shibahara, et al., "Implications of isoform multiplicity of microphthalmia-associated transcription factor in the pathogenesis of auditory-pigmentary syndromes", *J. Investig. Dermatol. Symp. Proc.*, 4(2):101-4 (1999).

Sorsby and Davey, "Ocular associations of dappling (or merling) in the coat colour of dogs. I. Clinical and genetical data", *J. Genet.*, 52:425-440 (1954).

Sponenberg & Bowling, "Heritable syndrome of skeletal defects in a family of Australian shepherd dogs", *J. Hered.*, 76(5):393-394 (1985).

Sponenberg, "Germinal reversion of the merle allele in Australian shepherd dogs", *J. Hered.*, 75(1):78 (1984).

Sponenberg, "Inheritance of the harlequin color in Great Dane dogs", *J. Hered.*, 76(3):224-5 (1985).

Steingrimsson, et al., "Melanocytes and the microphthalmia transcription factor network", *Annu. Rev. Genet.*, 38:365-411 (2004).

Sturm, et al., "Human pigmentation genes: identification, structure and consequences of polymorphic variation", *Gene*, 277(1-2):49-62 (2001).

Tassabehji, et al., "Waardenburg syndrome type 2 caused by mutations in the human microphthalmia (MITF) gene", *Nat. Genet.*, 8(3):251-255 (1994).

Tassabehji, et al., "Waardenburg's syndrome patients have mutations in the human homologue of the Pax-3 paired box gene", *Nature*, 355(6361):635-636 (1992).

Tatusova and Madden, "BLAST 2 Sequences, a new tool for comparing protein and nucleotide sequences", *FEMS Microbiol. Lett.*, 174(2):247-50 (1999). Erratum in: FEMS Microbiol. Lett. 177(1):187-8 (1999).

Tomita and Suzuki, "Genetics of pigmentary disorders", *Am. J. Med. Genet. C. Semin. Med. Genet.*, 131C(1):75-81 (2004).

Waardenburg, "A new syndrome combining developmental anomalies of the eyelids, eyebrows and nose root with pigmentary defects of the iris and head hair and with congenital deafness", *Am. J. Hum. Genet.*, 3(3):195-253 (1951).

Wang, et al., "PCR/RFLP Marker in the Canine Transducin-gamma Gene (GNGT1)," *Animal Genetics*, 28:319-320 (1997).

Whitney & Lamoreux, "Transposable-elements controlling genetic instabilities in mammals", *J. Hered.*, 73(1):12-18 (1982).

Zeiss, et al., "A highly polymorphic RFLP marker in the Canine Retinitis Pigmentosa GTPase Regulator (RPGR) gene," *Animal Genetics*, 29:409 (1998).

Sequence alignment: SEQ ID No. 799 aligned with EMBL Nucleotide Sequence Database, "Accession No. C01052", (1 page), Jul. 17, 1996.

Sequence alignment: SEQ ID No. 34, SEQ ID No. 35, and SEQ ID No. 36 aligned with EMBL Nucleotide Sequence Database, "Accession No. CE177786", (2 pages), Sep. 29, 2003.

\* cited by examiner

FIGURES 1A, 1B, AND 1C

```
MM Sheltie       TAGGGGAAGACCTCTTTTTTTTTTTTTTTTTTTTTTTTTTTTTTTTTTTTTTTTTTTTTT
Mm Sheltie       TAGGGGAAGACCTCTTTTTTTTTTTTTTTTTTTTTTTTTTTTTTTTTTTTTTTTTTTTT
Mm Collie        TAGGGGAAGACCTCTTTTTTTTTTTTTTTTTTTTTTTTTTTTTTTTTTTTTTTTTTTTT
Mm Border Collie TAGGGGAAGACCTCTTTTTTTTTTTTTTTTTTTTTTTTTTTTTTTTTTTTTTTTTTTT
Mm Aus. Shep.    TAGGCGAAGACCTCTTTTTTTTTTTTTTTCTTTTTTTTTTTTTTTTTTTTTTTTTTTT
Mm CW Corgi      TAGGGGAAGACCTCTTTTTTTTTTTTTTTTTTTTTTTTTTTTTTTTTTTTTTTTTTTT
Mm Dachshund     TAGGGGAAGACCTCTTTTTTTTTTTTTTTTTTTTTTTTTTCTTTTTTTTTTTTTTT
Mm Great Dane    TAGGGGAAGACCTCTTTTTTTTTTTCTTTTTTTTTTTTTTTTTTTTTTTTTTTTTT
mm Sheltie       TAGGCGAAGACTTCTTTTTTTTTTTTTTTTTTTTTTTTTTTTTTTTTTTTTTTT--
mm Sheltie       TAGGCGAAGACTTCTTTTTTTTTTTTTTTTTTTTTTTTTTTTTTTTTTTTTTTTT-
mm Great Dane    TAGGCGAAGACTTCTTTTTTTTTTTTTTTTTTTTTTTTTTTTTTTTTTTTT-----
                 ****  ******  *************  **  *************  ********

MM Sheltie       TTTTTTTTTTTTTTTTTTTTTTTTTTTT-----------AAATTTTTATTTATTTATGATA
Mm Sheltie       TTTTTTTTTTTTTTTTTTTTTTTTTTTTT--------AAATTTTTATTTATTTATGATA
Mm Collie        TTTTTTTTTTTTTTTTTTTTTTTTTTTTTTTTTTTTTTAAATTTTTATTTATTTATGATA
Mm Border Collie TTTTTTTTTTTTTTTTTTTTTTTTTTTTTT--AAATTTTTATTTATTTATGATA
Mm Aus. Shep.    TTTTTTTTTTTTTTTTTTTTTTTTTTTTT-----AAATTTTTATTTATTTATGATA
Mm CW Corgi      TTTTTTTTTTTTTTTTTTTTTTTTTTTTTTTT----AAATTTTTATTTATTTATGATA
Mm Dachshund     TTTTTTTTTTTTTTTTTTTTTTTTTTTTTTT-------AAATTTTTATTTATTTATGATA
Mm Great Dane    TTTTTTTTTTTTTTTTTTTTTTTTTTTTTTTT------AAATTTTTATTTATTTATGATA
mm Sheltie       --------------------------------------AAATTTTTATTTATTTATGATA
mm Sheltie       --------------------------------------AAATTTTTATTTATTTATGATA
mm Great Dane    --------------------------------------AAATTTTTATTTATTTATGATA
                                                       ************************

MM Sheltie       GTCACA--GAGAGAGAGAGAGGCGCAGAGACACAGGCAGAGGGAGAAGCAGGCTCCATGC
Mm Sheltie       GTCACAGAGAGAGAGAGAGAGAGGCGCAGAGACACAGGCAGAGGGAGAAGCAGGCTCCATGC
Mm Collie        GTCACAGAGAGAGAGAGAGAGAGGCGCAGAGACACAGGCAGAGGGAGAAGCAGGCTCCATGC
Mm Border Collie GTCACAGAGAGAGAGAGAGAGAGGCGCAGAGACACAGGCAGAGGGAGAAGCAGGCTCCATGC
Mm Aus. Shep.    GTCACAGAGAGAGAGAGAGAGAGGCGCAGAGACACAGGCAGAGGGAGAAGCAGGCTCCATGC
Mm CW Corgi      GTCACAGAGAGAGAGAGAGAGGCGCAGAGACACAGGCAGAGGGAGAAGCAGGCTCCATGC
Mm Dachshund     GTCACA--GAGAGAGAGAGAGGCGCAGAGACACAGGCAGAGGGAGAAGCAGGCTCCATGC
Mm Great Dane    GTCACACAGAGAGAGAGAGAGGCGCAGAGACACAGGCAGAGGGAGAAGCAGGCTCCATGC
mm Sheltie       GTCACAGAGAGAGAGAGAGAGAGGCGCAGAGACACAGGCAGAGGGAGAAGCAGGCTCCATGC
mm Sheltie       GTCACAGAGAGAGAGAGAGAGAGGCGCAGAGACACAGGCAGAGGGAGAAGCAGGCTCCATGC
mm Great Dane    GTCACAGAGAGAGAGAGAGAGGCGCAGAGACACAGGCAGAGGGAGAAGCAGGCTCCATGC
                 ******  ****************************************************

MM Sheltie       ACCGGGAGCCCGACGTGGGATTCGATCCCGGGTCTCCAGGATCGCGCCCTGGGCCAAAGG
Mm Sheltie       ACCGGGAGCCCGACGTGGGATTCGATCCCGGGTCTCCAGGATCGCGCCCTGGGCCAAAGG
Mm Collie        ACCGGGAGCCCGACGTGGGATTCGATCCCGGGTCTCCAGGATCGCGCCCTGGGCCAAAGG
Mm Border Collie ACCGGGAGCCCGGCGTGGGATTCGATCCCGGGTCTCCAGGATCGCGCCCTGGGCCAAAGG
Mm Aus. Shep.    ACCGGGAGCCCGACGTGGGATTCGATCCCGGGTCTCCAGGATCGCGCCCTGGGCCAAAGG
Mm CW Corgi      ACCGGGAGCCCGACGTGGGATTCGATCCCGGGTCTCCAGGATCGCGCCCTGGGCCAAAGG
Mm Dachshund     ACCGGGAGCCCGACGTGGGATTCGATCCCGGGTCTCCAGGATCGCGCCCTGGGCCAAAGG
Mm Great Dane    ACCGGGAGCCCGACGTGGGATTCGATCCCGGGTCTCCAGGATCGCGCCCTGGGCCAAAGG
mm Sheltie       ACCGGGAGCCCGACGTGGGATTCGATCCCGGGTCTCCAGGATCGCGCCCTGGGCCAAAGG
mm Sheltie       ACCGGGAGCCCGACGTGGGATTCGATCCCGGGTCTCCAGGATCGCGCCCTGGGCCAAAGG
mm Great Dane    ACCGGGAGCCCGACGTGGGATTCGATCCCGGGTCTCCAGGATCGCGCCCTGGGCCAAAGG
                 *********** *************************************************

MM Sheltie       CAGGCGCCAAACCGCTGCGCCACCCAGGGATCCC (SEQ ID NO: 26)
Mm Sheltie       CAGGCGCCAAACCGCTGCGCCACCCAGGGATCCC (SEQ ID NO: 27)
Mm Collie        CAGGCGCCAAACCGCTGCGCCACCCAGGGATCCC (SEQ ID NO: 28)
Mm Border Collie CAGGCGCCAAACCGCTGCGCCACCCAGGGATCCC (SEQ ID NO: 29)
Mm Aus. Shep.    CAGGCGCCAAACCGCTGCGCCACCCAGGGATCCC (SEQ ID NO: 30)
Mm CW Corgi      CAGGCGTCAAACCGCTGCGCCACCCAGGGATCCC (SEQ ID NO: 31)
Mm Dachshund     CAGGCGCCAAACCGCTGCGCCACCCAGGGATCCC (SEQ ID NO: 32)
Mm Great Dane    CAGGCGCCAAACCGCTGCGCCACCCAGGGATCCC (SEQ ID NO: 33)
mm Sheltie       CAGGCGCCAAACCGCTGCGCCACCCAGGGATCCC (SEQ ID NO: 34)
mm Sheltie       CAGGCGCCAAACCGCTGCGCCACCCAGGGATCCC (SEQ ID NO: 35)
mm Great Dane    CAGGCGCCAAACCGCTGCGCCACCCAGGGATCCC (SEQ ID NO: 36)
                 ******  ********************* ******
                    B Box                A Box
```

FIGURE 3

METHODS FOR IDENTIFICATION OF MERLE GENE

CROSS REFERENCE TO RELATED APPLICATIONS

This application is a filing under 35 U.S.C. 371 of PCT/US2006/032100 filed with the U.S. Receiving Office on Aug. 16, 2006, which claims the benefit of U.S. Ser. No. 60/708,589 filed in the U.S. Patent and Trademark Office on Aug. 16, 2005, all of which are incorporated by reference in their entirety.

BACKGROUND OF THE INVENTION

The present invention is generally in the field of genetic testing in dogs, and is specifically a genetic test for the gene that produces merle coat color.

Merle is a coat pattern in the dog characterized by patches of diluted pigment intermingled with normal melanin (FIG. 1B). It is a standard coloration for several breeds recognized by the American Kennel Club, including the Shetland Sheepdog, Collie, Border Collie, Australian Shepherd, Cardigan Welsh Corgi, and Dachshund. The merle phenotype in the Dachshund is also known as dapple. Although merle is not an acceptable color in the Great Dane, the desirable harlequin pattern results from the interaction of the merle locus (M) and a separate harlequin locus (H) (O'Sullivan, N., & Robinson, R. (1989) *Genetica* 78, 215-218). In addition, many breeds (e.g., Catahoula Leopard Dog, Norwegian Hound, and Pyrenean Shepherd) accepted by other kennel clubs present with merle patterning.

Merle is inherited in an autosomal, incompletely dominant fashion (Mitchell, A. L. (1935) *J. Hered.* 26, 425-430). Although rare, a dog carrying the merle allele (Mm) can appear to be nonmerle, which is know as "cryptic" merle, and produce merle offspring. Dogs homozygous for merle (MM) are known as double merles and are predominantly white (FIG. 1C).

Dogs having Mm and MM genotypes typically have blue eyes and can exhibit a wide range of auditory and opthalmologic abnormalities (Sorsby, A., & Davey, J. B. (1954) *J. Genet.* 54, 425-440). Reetz et al. studied the auditory capacity of dachshunds and found that 54.6% of MM and 36.8% of Mm dogs had auditory dysfunction, ranging from mild to severe deafness (Reetz, I., et al., (1977) *Disch. Tierarzil. Wschr.* 84, 273-277). All control dogs (mm) in the study had normal hearing. Klinckman et al. conducted opthalmologic studies with three groups of dachshunds (MM, Mm, and mm) and found that merles and double merles had significantly greater frequencies of ocular abnormalities, including increased intraocular pressure and ametropic eyes (Klinckmann, V. G., et al., (1987) *Disch. Tierarzil. Wschr.* 94, 338-341 and Klinckmann, V. G., & Wegner, W. (1987) *Disch. Tierarzil. Wschr.* 94, 337-338). Micropthalmia and colobomas are well described in merle and double merle dachshunds and Australian shepherds (Gelatt, K. N., & McGill, L. D. (1973) *J. Am. Vet. Med. Assoc.* 162, 393-396; Sorsby, A., & Davey, J. B. (1954) *J. Genet.* 54, 425-440; Dausch, D., et al., (1977) *Disch. Tierarzil. Wschr.* 84, 468-475). In all breeds, the double merle genotype can be sub-lethal and is associated with multiple abnormalities concerning the skeletal, cardiac, and reproductive systems (Sponenberg, D. P., & Bowling, A. T. (1985) *J. Hered.* 76, 393-394; Sponenberg, D. P., & Bowling, A. T. (1985) *J. Hered.* 76, 393-394., Little, C. C. (1957) *The Inheritance of Coat Color in Dogs*. Howell Book House Inc.). For these reasons, merle to merle breedings are not traditionally practiced (Little, C. C. (1957) *The Inheritance of Coat Color in Dogs*. Howell Book House Inc.).

It has been hypothesized that the merle locus contains a transposable element (Whitney, J. B., & Lamoreux, M. L. (1982) *J. Hered.* 73, 12-18). This hypothesis is based in part on the finding that matings of homozygous merle dogs have produced nonmerle offspring (Whitney, J. B., & Lamoreux, M. L. (1982) *J. Hered.* 73, 12-18 and Sponenberg, D. P. (1984) *J. Hered.* 75, 78). Subsequent breedings with these offspring produced only nonmerle puppies, providing evidence for a stable germinal reversion (Sponenberg, D. P. (1984) *J. Hered.* 75, 78).

Previously, candidate gene selection for merle has focused on genes implicated in similar coat patterning in mice and Waardenburg syndrome (WS) in humans (Schmutz, S. M., et al., (2002) *Anim. Genet.* 34, 65-77). WS is an autosomal dominant disorder associated with sensorineural hearing loss, pigmentary disturbances of the skin, hair, and eyes, and other developmental abnormalities (Waardenburg, P. J. (1951) *Am. J. Hum. Genet.* 3, 195-253). Several genes have been implicated in four clinical types of WS: mutations in PAX3 cause WS type 1 and type 3 (Baldwin, C. T., et al., (1992) *Nature* 355, 637-638 and Tassabehji, M., et al., (1992) *Nature* 355, 635-636) and mutations in SOX10, EDNRB, or EDNR3 cause WS type 4 (Pingault, V., et al., (1998) *Nat. Genet.* 18, 171-173; Puffenberger, E. G., et al., (1994) *Cell* 79, 1257-1266; and Mccallion, A. S., & Chakravarti, A. (2001) *Pigment Cell Res.* 14, 161-169). Mutations in MITF have been shown to cause WS type 2; however, the genetic basis for 85% of type 2 cases remains unidentified (Tassabehji, M., et al., (1994) *Nat. Genet*, 8, 251-255 and Choi, J. H., et al., (2004) *Korean J. Opthalmol.* 18, 185-189). Schaible and Brumbaugh (1976) suggest that the ultrastructure of abnormal tissues observed in WS is phenotypically similar to that present in merle dogs (Schaible, R. H., & Brumbaugh, J. A. (1976) *Pigment Cell* 3, 191-200).

While it is clear that there is a long felt need for a genetic test that permits the identification of animals with merle and "cryptic" merle genotypes, to date, the gene causative for merle has not been determined. If identified, the canine gene could be used to screen for a human homologue to determine if this gene is involved in auditory or ocular defects in humans.

It is therefore an object of the present invention to provide the gene mutation causative for merle coloration in the dog.

It is a further object of the present invention to provide methods for detecting mutations in the merle gene of the dog.

It is a further object of the present invention to provide methods for detecting mutations in the human homologue of the merle gene.

BRIEF SUMMARY OF THE INVENTION

Animals with mutations in SILV present with the merle coat color pattern phenotype. Methods for the identification of animals that harbor a mutation in the SILV gene are described in more detail below. This gene has been described in multiple organisms but never implicated as being involved in merle patterning. Example 1 demonstrates that dogs with mutations in SILV present with the merle coat color pattern phenotype. One such mutation is an insertion of a short interspersed nucleotide element ("SINE") into intron 10 of SILV and is present in multiple breeds of dogs. The insertion of the SINE into the SILV gene is thought to cause a splice site mutation resulting in an abnormal mRNA. Identification of the mutations in SILV gene allows owners or breeders to ascertain the genotype of animals as it pertains to merle. Such information is of great value when planning matings so that desired coat color patterns and animals without auditory and opthalmologic abnormalities are produced in offspring. A microsatellite marker that segregates with merle is also described that was identified using linkage disequilibrium mapping. Mutations in the SILV gene can be identified from any biological sample such as a cell or tissue that contains genomic DNA. Typical samples include hair roots or cheek swaps. One such mutation is an insertion of a SINE into intron 10 of SILV and is present in all breeds of dogs analyzed to date.

SILV may be involved in human deafness disorders, such as Waardenburg syndrome (WS). The SILV gene has been sequenced and described in the human and is present on HSA12. Therefore, analysis of human SILV in normal and WS patients can be accomplished by sequencing the gene from these individuals for any type of mutation, including insertion of SINEs and LINEs (Long Interspersed Nucleotide Elements), causative for the associated phenotype.

BRIEF DESCRIPTION OF THE DRAWINGS

FIG. 3 is the sequence alignment of the SINE insertion in 8 merle dogs from 7 breeds (Shetland Sheepdog "Sheltie," Collie, Border Collie, Australian Shepherd, Cardigan Welsh Corgi, Dachshund, and Great Dane) and 3 non-merle dogs from 2 breeds (Shetland Sheepdog and Great Dane) with the smaller insertion. Putative A and B boxes necessary for RNA polymerase III transcriptional control are shown in gray.

DETAILED DESCRIPTION OF THE INVENTION

Definitions

Figure 1:
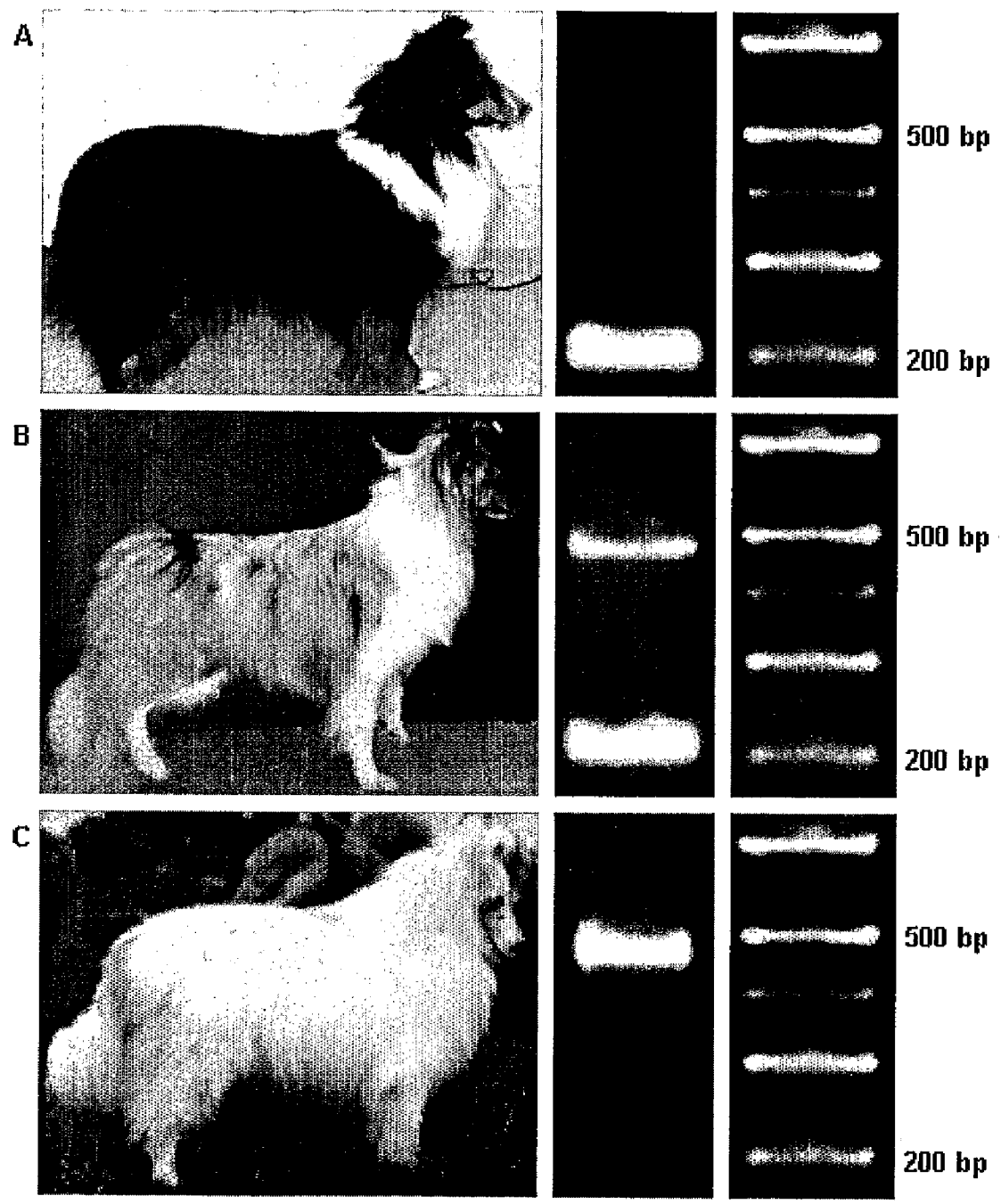
FIGS. 1A, 1B and 1C are photos of a normal non-merle, heterozygote merle, and double homozygous merle Shetland Sheepdog and DNA analysis for the merle SINE. The SINE insertion in SILV segregates with merle phenotype. (A) Tri-colored (black, sable, white), non-merle Shetland Sheepdog (mm) (B) Blue merle Shetland Sheepdog (Mm) and (C) Double merle Shetland Sheepdog (MM).

"Genetic marker" or "marker" as used herein refers to a variable nucleotide sequence (polymorphic) that is present in genomic DNA, and which is identifiable with specific oligonucleotides (e.g., distinguishable by nucleic acid amplification and observance of a difference in size or sequence of nucleotides due to the polymorphism). The "locus" of a genetic marker or marker refers to its place on the chromosome in relation to another locus. Markers, as illustrated herein, can be identified by any one of several techniques know to those skilled in the art, including microsatellite or short tandem repeat (STR) amplification, analyses of restriction fragment length polymorphisms (RFLP), single nucleotide polymorphism (SNP), detection of deletion or insertion sites, and random amplified polymorphic DNA (RAPD) analysis (Cushwa and Medrano, 1996, Animal Biotech. 7:11-31).

"Co-segregate" as used herein refers to inheritance together of two specific loci; e.g., the loci are located so physically close on the same chromosome that the rate of genetic recombination between the loci is low, as observed by statistical analysis of inheritance patterns of alleles in a mating.

"Linkage" as used herein refers to co-segregation of two loci in the canine breed analyzed.

"Linkage test" and "molecular diagnostic assay" are terms used herein to refer to a method for determining the presence or absence of one or more allelic variants linked with the SILV gene locus, such that the method may be used for the detection of SILV or carrier status, whether through statistical probability or by actual detection of a mutated SILV gene.

"Polymorphism" as used herein refers to a marker that is distinguishably different (e.g., in size, electrophoretic migration, nucleotide sequence, ability to specifically hybridize to an oligonucleotide under standard conditions) as compared to an analogous region from an animal of the same type or pedigree (i.e., family tree).

"Nucleic acid amplification" or "amplify" as used herein refers to a process by which nucleic acid sequences are amplified in number. There are several means known to those skilled in the art for enzymatically amplifying nucleic acid sequences including polymerase chain reaction ("PCR"), ligase chain reaction (LCR), and nucleic acid sequence-based amplification (NASBA) as discussed in more detail below.

"Hybridization" as used herein refers to a sufficient number of complementary base pairs in its sequence to interact specifically (hybridize) with the target nucleic acid sequence to be amplified or detected. As known to those skilled in the art, a very high degree of complementarity is needed for specificity and sensitivity involving hybridization, although it need not be 100%. Thus, for example, an oligonucleotide which is identical in nucleotide sequence to an oligonucleotide disclosed herein, except for a few base changes or substitutions, may function equivalently to the disclosed oligonucleotides.

"Cryptic" merle as used herein refers to an animal carrying the merle allele (Mm) which appears to be nonmerle but can produce merle offspring.

Merle Gene and Microsatellite Marker

In the dog, large areas of diluted pigment on a fully pigmented background is known as merle. The merle coat pattern is found in many canine breeds and is associated with multiple abnormalities.

A whole genome scan for linkage with merle using 40 Shetland sheepdogs showed Linkage Disequilibrium (LD) with FH2537 on CFA10. This region of CFA10 exhibits conservation of synteny with HSA12q13. No genes previously implicated in WS map to this region. Alternatively, a gene known as SILV that encodes a melanosomal protein maps to HSA12q13-q14 (Kwon, B. S., et al., (1991) *Proc. Natl. Acad. Sci. USA* 88, 9228-9232; Sturm, R. A., Teasdale, R. D., & Box, N. F. (2001) *Gene* 277, 49-62). SILV was shown to be important in melanogenesis when it was identified in the mouse as the silver locus that causes premature graying (Kwon, B. S., et al., (1995) Nucleic Acids Research 23, 154-

158), which is also characteristic of many WS patients (ref). The mutant phenotype of SILV in the human is unknown (Sturm, R. A., Teasdale, R. D., & Box, N. F. (2001) *Gene* 277, 49-62).

Merle Gene SINE

Based on LD data and the role of SILV in pigmentation, this gene was selected as a candidate for the merle locus. A SINE, structurally similar to a class of canine SINEs described by Minnick et al. (1992) *Gene* 110, 235-238), was identified in SILV for all merle dogs analyzed. This SINE shows high sequence similarity (95% to 97%) with canine SINEs previously identified in the canine D2 dopamine receptor gene (Jeoung, D., et al., (2000) *Anim. Genet.* 31, 334-335), the dystrophin gene (Fletcher, S., et al., (2000) *Am. J. Vet. Res.* 12, 1964-1968), and the PTPLA gene, implicated in centronuclear myopathy (Pele, M., et al., (2005) *Hum. Mol. Genet.* 14, 1417-1427). These SINEs are tRNA-derived and highly abundant in the dog, representing 7% of the genome (Kirkness, E. F., et al., (2003) *Science* 301, 1898-1903).

The pigmentation gene SILV (SEQ ID NO:1, shown below) was identified and evaluated as a candidate gene for merle patterning.

```
Canine Silver cDNA
                                             (SEQ ID NO: 1)
ATGGTACCTTCGTTTTTAGGACCCAGAGACCAGGACTGGCTTGGTGTCCC

AAGGCAGCTCACAACTAAAGCCTGGAACAGACAGCTGTATCCAGAGTGGA

CAGAAACCCAGAGGCCTGACTGCTGGAGAGGTGGGAACTTGGCAATTTCC

AGGGAGGGTGGCCAGGTGTCCCTGAAGGTCAGTAATGATGGGCCTACACT

GGTTGGTGCAAATGCCTCCTTCTCTATTGCCCTGCACTTCCCTGAAAGCC

AAAAGGTACTGCCAGATGGGCAGGTTGTCTGGGCCAACAACACTATCATC

GATGGGAGCCAGGTGTGGGGAGGACAGCCAGTGTATCCCCAGGTACTTGA

TGATGCCTGCATCTTCCCTGATGGGAGGGCCTGCCCATCTGGCCCTTGGT

CTCAGACAAGAAGCTTTGTTTATGTCTGGAAGACCTGGGTGTCTGGGCTG

AGCATTGTGACAGGCAAGGCGGTGCTGGGCACACATACCATGGAAGTGAC

TGTCTACCACCGCCGGGAGTCCCAGAGCTACGTGCCCCTTGCTCACTCCT

GCTCAGCCTTCACCATTACTGACCAGGTGCCCTTCTCCGTGAGTGTGTCT

CAGCTGCAGGCCTTGGATGGAGGGAACAAGCATTTCCTGAGAAATCATCC

TCTGACCTTTGCCCTCCGGCTCCATGACCCCAGCGGCTATTTGTCTGGGG

CTGACCTCTCCTACACCTGGGACTTTGGAGACCATACCGGGACCCTGATC

TCTCGGGCACTTGTGGTCACTCACACTTACCTAGAGTCTGGCCCAATCAC

TGCCCAGGTGGTCCTGCAGGCTGCCATTCCTCTCACTTCCTGTGGCTCCT

CCCCAGTTCCAGTCACCACAGATGGGCATGCGCCAACTGCAGAGATCCCT

GGCACCACAGCTGGGCGAGTGCCTACTGCAGAAGTCATAAAGCCCTCTGG

AACCACAGGCGAGCAGGTAACGACTAAAGAGTCAGTGGAGCCCACAGCTG

GAGAGGGACCCACGCCTGAGACCAAGGGTCCAGATACCAATCTGTTCGTG

CCTACAGAAGGTATTACAGGTTCCCAGAGCGCCCTGCTGGATGGCACAGC

TACCTTAATCCTGGCAAAGCGAGAAACCCCCCTGGATTGTGTTCTGTATC

GATATGGCTCCTTTTCTCTCACCCTGGACATTGTCCGGGGTATTGAGAAT

GCTGAGATCCTGCAGGCTGTGCCATCCAGTGAAGGGGATGCATTTGAGCT
```

-continued
```
GACTGTGTCTTGCCAAGGCGGACTGCCCAAGGAAGCCTGCATGGACATCT

CATCACCAGGGTGCCAGCCCCCTGCCCAGAGGCTATGTCAGCCTGTGCCG

CCCAGCCCAGCCTGCCAGCTGGTTTTGCACCAAGTGCTGAAGGGTGGCTC

AGGGACCTACTGCCTCAATGTGTCTTTGGCTGATGCTAACAGTCTGGCAA

TGGTCAGCACTCAGCTTGTAATGCCTGGTCAAGAAGCAGGCGTTGGACAG

GCTCCCCTGTTCATGGGCATCTTGCTGGTGTTGCTGGCTATGGTGCTGGT

ATCTCTGATATATAGGTGA
```

Figure 2:
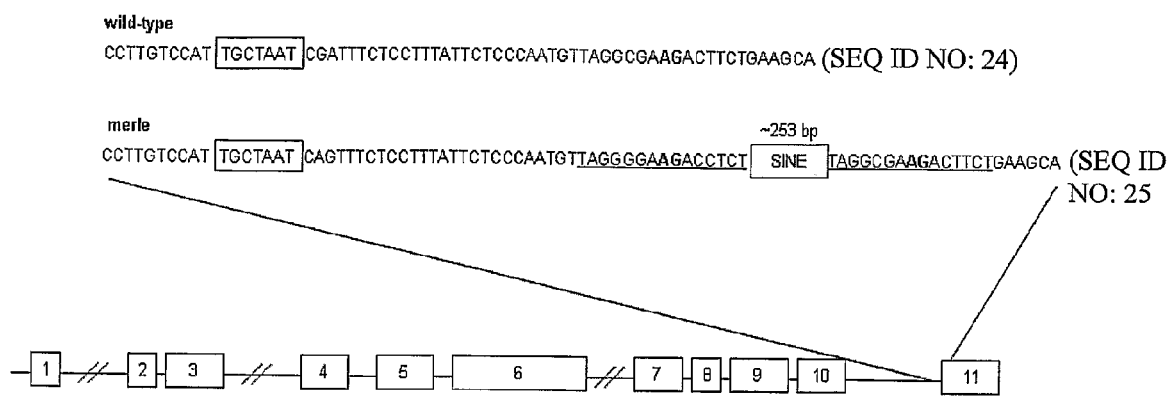
FIG. 2 depicts the structure of wild-type canine SILV and sequence of the SINE insertion site in merle dogs. The putative lariat branch point sequence is boxed. Splicing acceptors are indicated by bold type. In merle dogs, the splicing acceptor is located in the 15 base pair ("bp") duplicated sequence (underlined) that flanks the SINE mutation. The average insertion size (not including the duplicated sequence) for the merle dogs analyzed herein is 253 bp.

A SINE insertion at the intron 10/exon 11 boundary was found to segregate with the merle phenotype in multiple breeds. The SINE insertion reported herein also occurs at an intron/exon boundary and may displace the putative lariat branch point sequence (FIG. 2). Sequence of the SINE insertion in 7 breeds is shown in FIG. 3. Interestingly, some dogs have shortened versions of the SINE insertion and this has a dramatic effect on expression of the merle phenotype. Specifically, these dogs have deletions (ranging from 39 to 47 bp) within the poly-A of the SINE and do not have merle patterning.

Deletions within the poly-A segment of the SINE insertion in SILV may result in normal phenotype. The exact number of repeats needed to retain the merle phenotype is unknown. It is known that a deletion of approximately 30 bp from the poly-A results in non-merle phenotype. The poly-A segment is difficult to sequence, thus an accurate threshold for the length of the poly-A has not yet been determined.

The nucleic acid molecules or fragments need not be identical to the sequence of SEQ. ID. No. 25. Suitable nucleic acid molecules may be identified by hybridization to the nucleic acid sequence of the gene encoding canine merle, preferably SEQ. ID. No. 25. In a preferred embodiment, a suitable nucleic acid molecule hybridizes to the nucleic acid sequence of the gene under stringent conditions. For example, sequences can be isolated that hybridize to a DNA molecule comprising a nucleotide sequence of 50 continuous bases of SEQ. ID. No. 25 under stringent conditions characterized by a hybridization buffer comprising 0.9M sodium citrate ("SSC") buffer at a temperature of 37° C. and remaining bound when subject to washing with the SSC buffer at 37° C., and preferably in a hybridization buffer comprising 20% formamide in 0.9M saline/0.09M SSC buffer at a temperature of 42° C. and remaining bound when subject to washing at 42° C. with 0.2.times.SSC buffer at 42° C. In a preferred embodiment, these hybrizing nucleic acid molecules may be 10, 20, 30, 40, 50, 60, 70, 80, 90, 100 or some intermediate in length.

Merle Gene Microsatellite Marker

A microsatellite marker identified using linkage disequilibrium mapping that segregates with the SILV gene is also described. As described in detail below, linkage disequilibrium was identified with the merle phenotype in the Shetland sheepdog and a microsatellite marker located in a region of CFA10 that exhibits conservation of synteny with HSA12q13.

Methods for Determining Linkage

Linkage is the coinheritance of two or more nonallelic genes because their loci are in close proximity on the same chromosome, such that after meiosis they remain associated more often than the 50% expected for unlinked genes. During meiosis, there is a physical crossing over of genetic material, it is clear that during the production of germ cells there is a physical exchange of maternal and paternal genetic contributions between individual chromatids. This exchange necessarily separates genes in chromosomal regions that were contiguous in each parent and, by mixing them with retained linear order, results in "recombinants". The process of forming recombinants through meiotic crossing-over is an essential feature in the reassortment of genetic traits and is central to understanding the transmission of genes.

Recombination generally occurs between large segments of DNA. This means that contiguous stretches of DNA and genes are likely to be moved together. Conversely, regions of the DNA that are far apart on a given chromosome are more likely to become separated during the process of crossing-over than regions of the DNA that are close together.

The pattern of a set of markers along a chromosome is referred to as a "Haplotype". Therefore sets of alleles on the same small chromosomal segment tend to be transmitted as a block through a pedigree. By analyzing the haplotypes in a series of offspring of parents whose haplotypes are known, it is possible to establish which parental segment of which chromosome was transmitted to which child. When not broken up by recombination, haplotypes can be treated for mapping purposes as alleles at a single highly polymorphic locus.

The existence of a preferential occurrence of a disease gene in association with specific alleles of linked markers, such as single nucleotide polymorphisms (SNPs) or microsatellites, is called "Linkage Disequilibrium" (LD). This sort of disequilibrium generally implies that most chromosomes carry the same mutation and the markers being tested are very close to the gene carrying the mutation. By using a combination of several markers surrounding the presumptive location of the gene, a haplotype can be determined for affected and unaffected animals.

For any single gene disorder, identification of the defective gene can allow for screening of the at-risk population to identify carriers in an effort to reduce the frequency of the single gene disorder in that population. Linkage analysis is based on first finding the general chromosomal region in which the mutated gene is located, followed by identification of genetic markers to characterize a much smaller region of the chromosome containing the disease locus (the location of the mutated gene). The closer together the marker and the mutated gene are on the chromosome, the less likely a recombination event will occur between them during meioses; i.e., there is linkage between the marker and the mutated gene. The more closely linked the marker and mutated gene are, the more predictive and useful is the test for identifying carriers. Additionally, by using two or more marker loci, substantial additional information can be ascertained in a linkage analysis that can markedly increase the accuracy of the linkage test. For example, using multiple marker loci in a linkage analysis allows for the ability to screen various affected breeds of dogs to identify breed-specific haplotypes that characterize the SILV allele in the specific breed of dog. Markers additional to those in the examples disclosed herein, that map either by linkage or by physical methods so close to the SILV gene locus that any polymorphism in or with such derivative chromosomal regions, may be used in a molecular diagnostic assay for detection the carrier status of SILV.

Methods for Screening for Merle Genotype

The SILV gene can be screened for any type of mutation by numerous methods well known to one of ordinary skill in the art, as described above. In a preferred embodiment, the method for determining the genotype of an animal as it applies to the merle gene is a PCR-based test followed by gel electrophoresis. For example, DNA is extracted from cheek swabs taken from dogs. The DNA is amplified by PCR using primers that hybridize to the SILV gene. The resulting amplified DNA fragments are resolved by electrophoresis revealing different sized fragments, the larger of which harbors the SINE mutation in the SILV gene. This method can be performed in less than two days.

Other approaches to reveal the presence of the SINE in the SILV gene include, but are not limited to, Southern blotting using probes to the region of interest; fluorescently labeled primers that amplify the region of interest which is then analyzed using automated technology; different primers that bracket the region of interest.

The microsatellite is linked to the presence of the SINE insertion. The microsatellite marker will not be able to distinguish for merle dogs and non-merle dogs carrying insertion with deletions in the poly-A segment. Sequence analysis must be carried out to look at the length of Poly-A segment. Once a threshold for the length is established an "A count" would be the determining factor of whether a dog is merle or not. Presence of the deleted SINE insertion also has implications for future breedings with that dog. A dog carrying a deleted version of the SINE still maintains the risk of producing a merle offspring. This is extremely important if the dog is being bred to another merle dog.

Methods of using genetic markers, for determining whether an animal has a mutated SILV gene locus in one or both alleles and methods for identification of animals that harbor a mutation in the SILV gene are described in more detail below.

Biological Samples to be Screened

In a preferred embodiment, the biological sample is any tissue containing genomic DNA. Most preferably, the biological sample is blood, hair, mucosal scrapings, semen, tissue biopsy, or saliva. In a most preferred embodiment, the biological sample is blood.

Methods of screening a biological sample for mutated nucleic acids can be carried out using either deoxyribonucleic acids ("DNA") or messenger ribonucleic acids ("mRNA") isolated from the biological sample. During periods when the gene is expressed, mRNA may be abundant and more readily detected. However, these genes are temporally controlled and, at most stages of development, the preferred material for screening is DNA.

Nucleic acid Reagents and Methods

The reagents typically consist of oligonucleotides that identify either the:

(1) SINE inserted into the SILV gene; or
(2) microsatellite marker associated with the SINE inserted into the SILV gene; and optionally,
(3) the polymorphisms associated with the SINE inserted into the SILV gene that result in a normal phenotype.

The SINE insertion reported herein occurs at an intron/exon boundary and may displace the putative lariat branch point sequence (FIG. 2). The variations in the length of poly-A segment may allow for proper placement of lariat branch point and thus result in non-merle phenotype.

The nucleic acid molecules may be linked to other nucleic acid molecules such as vectors or tags to facilitate amplification, purification, or identification. These may be used in any of the following assays or others used by those skilled in the art for genetic analysis.

Oligonucleotide Ligation Assay ("OLA") (Landegren et el., "A Ligase-Mediated Gene Detection Technique," Science, 241:1077-1080 (1988); Landegren et al., "DNA Diagnostics—Molecular Techniques and Automation," Science, 242:229-237 (1988); U.S. Pat. No. 4,988,617 to Landegren et al.), is one method for testing the genetic material in the biological sample. The OLA protocol uses two oligonucleotides which are designed to be capable of hybridizing to abutting sequences of a single strand of a target. One of the oligonucleotides is biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. OLA is capable of detecting insertion mutations. However, numerous methods for characterizing or detecting insertion mutations are known in the art and any of those methods are also suitable.

Another method of characterizing an insertion mutation entails direct DNA sequencing of the genetic locus that flanks and includes the insertion. Such analysis can be accomplished using either the "dideoxy-mediated chain termination method," also known as the "Sanger Method" (Sanger et al., "DNA Sequencing with Chain-Terminating Inhibitors," Proc. Natl. Acad. Sci. USA, 74:5463-5467 (1977)) or the "chemical degradation method," also known as the "Maxam-Gilbert method" (Maxam et al., "A New Method for Sequencing DNA," Proc. Natl. Acad. Sci. USA, 74:560-564 (1977)).

One example of a procedure for sequencing DNA molecules using arrays of oligonucleotides is disclosed in U.S. Pat. No. 5,202,231 to Drmanac et al. This involves application of target DNA to a solid support to which a plurality of oligonucleotides are attached. Sequences are read by hybridization of segments of the target DNA to the oligonucleotides and assembly of overlapping segments of hybridized oligonucleotides. The array utilizes all possible oligonucleotides of a certain length between 11 and 20 nucleotides, but there is little information about how this array is constructed. See also Chetverin et al., "Sequencing of Pools of Nucleic Acids on Oligonucleotide Arrays," BioSystems 30: 215-31 (1993); WO 92/16655 to Khrapko et al.; Kuznetsova et al., "DNA Sequencing by Hybridization with Oligonucleotides Immobilized in Gel. Chemical Ligation as a Method of Expanding the Prospects for the Method," Mol. Biol. 28(20): 290-99 (1994); Livits et al., "Dissociation of Duplexes Formed by Hybridization of DNA with Gel-Immobilized Oligonucleotides," J. Biomolec. Struct. & Dynam. 11(4): 783-812 (1994).

WO 89/10977 to Southern, discloses the use of a support carrying an array of oligonucleotides capable of undergoing a hybridization reaction for use in analyzing a nucleic acid sample for known point mutations, genomic fingerprinting, linkage analysis, and sequence determination. The matrix is formed by laying nucleotide bases in a selected pattern on the support. This reference indicates that a hydroxyl linker group can be applied to the support with the oligonucleotides being assembled by a pen plotter or by masking.

Single strand polymorphism assay ("SSPA") analysis and the closely related heteroduplex analysis methods are methods for screening for single-base mutations (Orita et al., "Detection of Polymorphisms of Human DNA by Gel Electrophoresis as Single-Strand Conformation Polymorphisms," Proc. Natl. Acad. Sci. USA, 86:2766-2770 (1989)). In these methods, the mobility of PCR-amplified test DNA from clinical specimens is compared with the mobility of DNA amplified from normal sources by direct electrophoresis of samples in adjacent lanes of native polyacrylamide or other types of matrix gels. Single-base changes often alter the secondary structure of the molecule sufficiently to cause slight mobility differences between the normal and mutant PCR products after prolonged electrophoresis.

Ligase chain reaction is another method of screening for mutated nucleic acids (see Barany, "Genetic Disease Detection and DNA Amplification Using-Cloned Thermostable Ligase," Proc. Natl. Acad. Sci. USA, 88:189-193 (1991); Barany, "The Ligase Chain Reaction (LCR) in a PCR World," PCR Methods and Applications, 1:5-16 (1991); WO 90/17239 to Barany et al.; Barany et al., "Cloning, Overexpression and Nucleotide Sequence of a Thermostable DNA Ligase-Encoding Gene," Gene, 109:1-11 (1991); and Barany, "Genetic Disease Detection and DNA Amplification Using Cloned Thermostable Ligase," Proc. Natl. Acad. Sci. USA, 88:189-193 (1991). In general, the LCR procedure is carried out with two pairs of oligonucleotide probes: one pair binds to one strand of the target sequence to be detected; the other pair binds to the other complementary strand of the target sequence to be detected. The reaction is carried out by denaturing the strands of the target sequence, then reacting the separated strands with the two pairs of oligonucleotide probes in the presence of a heat stable ligase so that each pair of oligonucleotide probes hybridizes to target DNA and, if there is perfect complementarity at their junction, adjacent probes are ligated together. If such complementarity is lacking, no ligation occurs and the probes separate individually from the target sequence during denaturation. The ligated or unligated probes are then separated during the denaturation step. The process is cyclically repeated until the sequence has been amplified to the desired degree. Detection can then be carried out by electrophoresis or by capture hybridization on an array of DNA probes. Ligated and unligated probes can then be detected to identify the presence of a mutation.

The ligase detection reaction (LDR) process is another method for detecting a mutation described generally in WO 90/17239 to Barany et al., Barany et al., "Cloning, Overexpression and Nucleotide Sequence of a Thermostable DNA Ligase-encoding Gene," Gene, 109:1-11 (1991), and Barany, "Genetic Disease Detection and DNA Amplification Using Cloned Thermostable Ligase," Proc. Natl. Acad. Sci. USA, 88:189-193 (1991). The ligase detection reaction is similar to the LCR technique; however, in LDR, there is only one pair of oligonucleotide probes which are complementary to one strand of the target sequence. While LCR provides an opportunity for exponential amplification, LDR achieves linear amplification.

Mundy et al. (U.S. Pat. No. 4,656,127) discusses alternative methods for determining the identity of the nucleotide present at a particular polymorphic site. Mundy's methods employ a specialized exonuclease-resistant nucleotide derivative. A primer complementary to the allelic sequence immediately 3'-to the polymorphic site is permitted to hybridize to a target molecule obtained from a particular animal or human. If the polymorphic site on the target molecule contains a nucleotide that is complementary to the particular exonucleotide-resistant nucleotide derivative present, then that derivative will be incorporated by a polymerase onto the end of the hybridized primer. Such incorporation renders the primer resistant to exonuclease, and thereby permits its detection. Since the identity of the exonucleotide-resistant derivative of the sample is known, a finding that the primer has become resistant to exonucleases reveals that the nucleotide present in the polymorphic site of the target molecule was complementary to that of the nucleotide derivative used in the reaction. Several primer-guided nucleotide incorporation procedures, for assaying polymorphic sites (i.e., sites of mutations) in DNA have been described (Kornher et al., "Mutation Detection Using Nucleotide Analogs that Alter Electrophoretic Mobility," Nucl. Acids. Res., 17:7779-7784 (1989); Sokolov, "Primer Extension Technique for the Detection of Single Nucleotide in Genomic DNA," Nucl. Acids Res., 18:3671 (1990); Syvanen et al., "A Primer-Guided Nucleotide Incorporation Assay in the Genotyping of Apolipoprotein E," Genomics, 8:684-692 (1990); Kuppuswamy et al., "Single Nucleotide Primer Extension to Detect Genetic Diseases: Experimental Application to Hemophilia B (Factor IX) and Cystic Fibrosis Genes," Proc. Natl. Acad. Sci. USA, 88:1143-1147 (1991); Prezant et al., "Trapped-Oligonucleotide Nucleotide Incorporation (TONI) Assay, a Simple Method for Screening Point Mutations," Hum. Mutat., 1:159-164 (1992); Ugozzoli et al., "Detection of Specific Alleles by Using Allele-specific Primer Extension Followed by Capture on Solid Support," GATA, 9:107-112 (1992); Nyren et al., "Solid Phase DNA Minisequencing by an Enzymatic Luminometric Inorganic Pyrophosphate Detection Assay," Anal. Biochem., 208:171-175 (1993). These methods differ from Genetic Bit Analysis™ ("GBA™" discussed extensively below) in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen et al., "Identification of Individuals by Analysis of Biallelic DNA Markers, Using PCR and Solid-Phase Minisequencing," Amer. J. Hum. Genet., 52:46-59 (1993)).

Cohen et al. (French Patent 2,650,840; PCT Application No. WO 91/02087, discusses a solution-based method for determining the identity of the nucleotide of a polymorphic site. As in the Mundy method of U.S. Pat. No. 4,656,127, a primer is employed that is complementary to allelic sequences immediately 3'-to a polymorphic site. The method determines the identity of the nucleotide of that site using labeled dideoxynucleotide derivatives, which, if complementary to the nucleotide of the polymorphic site, will become incorporated onto the terminus of the primer.

An alternative method, known as Genetic Bit Analysis™ or GBA™ is described by Goelet et al. PCT Publication No. WO 92/15712. In a preferred embodiment, the method of Goelet et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. French Patent 2,650,840; PCT Publication No. WO 91/02087, the method of Goelet et al. is preferably a heterogeneous phase assay, in which the primer or the target molecule is immobilized to a solid phase.

Other methods for detecting the presence of mutations include: differential restriction endonuclease digestion (DRED), allele-specific oligonucleotide probing (ASOP), and ligase-mediated gene detection (LMGD). Additional methods of analysis could also be useful in this context, such as fluorescence resonance energy transfer (FRET) as disclosed by Wolf et al., "Detection of Nucleic Acid Hybridization by Nonradiative Fluorescence Resonance Energy Transfer," Proc. Nat. Acad. Sci. USA, 85: 8790-94 (1988).

DRED analysis is accomplished in the following manner. If conditions occur including (1) a particular amplified cDNA segment contains a sequence variation that distinguishes an allele of a polymorphism and (2) this sequence variation is recognized by a restriction endonuclease, then the cleavage by the enzyme of a particular polynucleotide segment can be used to determine the alloantigen phenotype. In accomplishing this determination, amplified cDNA derived from platelet or red blood cell mRNA is digested and the resulting fragments are analyzed by size. The presence or absence of nucleotide fragments, corresponding to the endonuclease-cleaved fragments, determines which phenotype is present.

In ASOP analysis according to conventional methods, oligonucleotide probes are synthesized that will hybridize, under appropriate annealing conditions, exclusively to a particular amplified cDNA segment that contains a nucleotide sequence that distinguishes one allele from other alleles of a red blood cell or platelet membrane glycoprotein. This specific probe is discernibly labeled so that when it hybridizes to the allele distinguishing cDNA segment, it can be detected, and the specific allele is thus identified.

In LMGD, as disclosed by Landegren et al., "A Ligase-Mediated Gene Detection Technique," Science, 241: 1077-80 (1988), a pair of oligonucleotide probes are synthesized that will hybridize adjacently to each other, i.e., to a cDNA segment under appropriate annealing conditions, at the specific nucleotide that distinguishes one allele from other alleles. Each of the pair of specific probes is labeled in a different manner, and when it hybridizes to the allele-distinguishing cDNA segment, both probes can be ligated together by the addition of a ligase. When the ligated probes are isolated from the cDNA segments, both types of labeling can be observed together, confirming the presence of the allele-specific nucleotide sequence. Where the above-described pair of differently labeled probes bind to a nucleotide sequence containing a distinguishing nucleotide of a different allele, the probe pair is not ligatable and, after the probes are isolated from the cDNA segments, both types of labeling are observed separately.

WO 94/11530 to Cantor, relates to the use of an oligonucleotide array to carry out a process of sequencing by hybridization. The oligonucleotides are duplexes having overhanging ends to which target nucleic acids bind and are then ligated to the non-overhanging portion of the duplex. The array is constructed by using streptavidin-coated filter paper which captures biotinylated oligonucleotides assembled before attachment.

WO 93/17126 to Chetverin, uses sectioned, binary oligonucleotide arrays to sort and survey nucleic acids. These arrays have a constant nucleotide sequence attached to an adjacent variable nucleotide sequence, both bound to a solid support by a covalent linking moiety. The constant nucleotide sequence has a priming region to permit amplification by PCR of hybridized strands. Sorting is then carried out by hybridization to the variable region. Sequencing, isolating, sorting, and manipulating fragmented nucleic acids on these binary arrays are also disclosed. In one embodiment with enhanced sensitivity, the immobilized oligonucleotide has a shorter complementary region hybridized to it, leaving part of the oligonucleotide uncovered. The array is then subjected to hybridization conditions so that a complementary nucleic acid anneals to the immobilized oligonucleotide. DNA ligase is then used to join the shorter complementary region and the complementary nucleic acid on the array.

WO 92/10588 to Fodor et al., discloses a process for sequencing, fingerprinting, and mapping nucleic acids by hybridization to an array of oligonucleotides. The array of oligonucleotides is prepared by a very large scale immobilized polymer synthesis which permits the synthesis of large, different oligonucleotides. In this procedure, the substrate surface is functionalized and provided with a linker group by which oligonucleotides are assembled on the substrate. The regions where oligonucleotides are attached have protective groups (on the substrate or individual nucleotide subunits) which are selectively activated. Generally, this involves imaging the array with light using a mask of varying configuration so that areas exposed are deprotected. Areas which have been deprotected undergo a chemical reaction with a protected nucleotide to extend the oligonucleotide sequence where imaged. A binary masking strategy can be used to build two or more arrays at a given time. Detection involves positional localization of the region where hybridization has taken place. See also U.S. Pat. Nos. 5,324,633 and 5,424,186 to Fodor et al., U.S. Pat. Nos. 5,143,854 and 5,405,783 to Pirrung et al., WO 90/15070 to Pirrung et al., Pease et al., "Light-generated Oligonucleotide Arrays for Rapid DNA Sequence Analysis", Proc. Natl. Acad. Sci. USA 91: 5022-26 (1994). Beattie et al., "Advances in Genosensor Research," Clin. Chem. 41(5): 700-09 (1995), discloses attachment of previously assembled oligonucleotide probes to a solid support.

Landegren et al., "Reading Bits of Genetic Information: Methods for Single-Nucleotide Polymorphism Analysis," Genome Research, 8:769-776 (1998), discloses a review of methods for mutation analysis.

In another embodiment, testing the biological sample includes amplifying a region of the merle gene to provide an amplified fragment before detecting any mutation present in the biological sample.

Amplification of a selected, or target, nucleic acid sequence may be carried out by any suitable means, either to facilitate sequencing or for direct detection of mutations. (See generally Kwoh et al., "Target Amplification Systems in Nucleic Acid-Based Diagnostic Approaches," Am. Biotechnol. Lab., 8:14-25 (1990)) Examples of suitable amplification techniques include, but are not limited to, polymerase chain reaction, ligase chain reaction ("LCR") strand displacement amplification (see generally, Walker et al., "Strand Displacement Amplification—An Isothermal, In Vitro DNA Amplification Technique," Nucleic Acids Res., 20:1691-1696 (1992); Walker et al., "Isothermal In-Vitro Amplification of DNA By a Restriction Enzyme-DNA Polymerase System," Proc. Natl. Acad. Sci. USA 89:392-396 (1992), transcription-based amplification (see Kwoh et al., "Transcription-Based Amplification System and Detection of Amplified Human Immunodeficiency Virus Type 1 With a Bead-Based Sandwich Hybridization Format," Proc. Natl. Acad. Sci. USA 86:1173-1177 (1989)), self-sustained sequence replication (or "3SR") (see Guatelli et al., "Isothermal In-Vitro Amplification of Nucleic Acids By a Multienzyme Reaction Modeled After Retroviral Replication," Proc. Natl. Acad. Sci. USA 87:1874-1878 (1990)), the Qβ replicase system (see Lizardi et al., "Exponential Amplification of Recombinant RNA Hybridization Probes," Biotechnology, 6:1197-1202 (1988)), nucleic acid sequence-based amplification (or "NASBA"), the repair chain reaction (or "RCR"), and boomerang DNA amplification (or "BDA") (see Lewis, "Review of Progress in Developing Amplification Technologies Which May Compete With Roche Diagnostic Systems' Polymerase Chain Reaction (PCR)," Genetic Engineering News, 12(9):1, 8-9 (1992)). Polymerase chain reaction is currently preferred.

Genomic sequence-specific amplification technologies, such as the polymerase chain reaction (Mullis et al., "Specific Enzymatic Amplification of DNA in Vitro the Polymerase Chain Reaction," Cold Spring Harbor Symp. Quant. Biol. 51:263-274 (1986); European Patent Application No. 50,424 to Erlich et al.; European Patent Application No. 84,796 to Erlich et al.; European Patent Application 258,017 to Erlich et al.; European Patent Application No. 237,362 to Erlich et al.; European Patent Application No. 201,184 to Mullis; U.S. Pat. No. 4,683,202 to Mullis et al.; U.S. Pat. No. 4,582,788 to Erlich; Saiki et al., "Enzymatic Amplification of Beta Globin Genomic Sequences and Restriction Site Analysis for Diagnosis of Sickle Cell Anemia," Science 230:1350-1354 (1985); and U.S. Pat. No. 4,683,194 to Saiki et al.), may be employed to facilitate the recovery of the desired polynucleotides. In this method, primers complementary to opposite end portions of the selected sequence(s) are used to promote, in conjunction with thermal cycling, successive rounds of primer-initiated replication. The amplified sequence may be readily identified by a variety of techniques. This approach is particularly useful for detecting the presence of low-copy sequences in a polynucleotide-containing sample, e.g., for detecting pathogen sequences in a body-fluid sample.

Testing the biological sample includes performing PCR using genomic DNA templates and polyacrylamide gel electrophoresis (PAGE). In particular, PCR is performed using primers spanning the location of the mutation. The sizes of the amplified DNA fragments from homozygous normal and affected dogs are different. Subsequently, the amplified DNA fragments are electrophoresed using PAGE. In one embodiment, the testing of the genetic material in the biological sample is carried out by Taq cycle sequencing. The method for cycle sequencing, based on linear amplification of template DNA by polymerase chain reaction, was described by Murray, "Improved Double Stranded Sequencing Using the Linear Polymerase Chain Reaction," Nucleic Acids Research, 17:88-89 (1989). This technique essentially combines thermocycling procedure using Taq polymerase with dideoxy sequencing. In principle, the sequencing reaction consists of primer annealing to the template DNA followed by repeated extension of the primer by Taq polymerase in the presence of dNTPs/ddNTPs, linearly amplifying the sequence reaction products. Currently, cycle sequencing is done almost exclusively by non-isotopic methods using an automated DNA sequencer. A popular format for the sequencing protocol developed by Probe et al., "A System for Rapid DNA Sequencing with Fluorescent Chain-Terminating Dideoxynucleotides," Science, 238:336-341 (1987), is based on the use of a set of four chain-terminating dideoxynucleotides, each coupled to a different fluorescent dye and distinguishable by fluorescence emission. The DNA fragments are resolved by gel electrophoresis in one sequencing lane and detected by a scanning fluorescence detection system with computer-based automatic sequence identification.

One method that can be used to detect a mutation is polymerase chain reaction restriction fragment length polymorphism (PCR-RFLP). Single nucleotide changes in the genes are common phenomenon. Such alterations, depending on their locations, can be innocuous or deleterious to the gene function. Single base changes can alter the recognition sequence of restriction enzymes resulting in creation of a new, or abolition of an existing, restriction site, giving rise to variation in DNA fragment length. The variants are called restriction fragment length polymorphism (RFLP). These are inherited in a codominant fashion and are allelic variants, generating homozygous and heterozygous genotypes. Identification of RFLP in mammalian genome has been classically determined by Southern blot analysis. Use of polymerase chain reaction (PCR) to detect RFLP has dramatically accelerated the pace of initial identification and subsequent assaying of a large number of samples in an easy to use format. In short, two oligonucleotide primers are designed from the region of the genome flanking the suspected variation in the sequence between two alleles. These primer pairs are used to amplify the encompassing region of interest from genomic DNA by PCR using Taq polymerase and dNTPs in the presence of an optimal concentration of magnesium chloride. The PCR products are digested with the restriction enzyme with altered recognition sites between two alleles of the genome, and the digested DNA fragments are separated by electrophoresis in a solid matrix of choice (e.g., agarose or polyacrylamide) depending on the size of the fragments.

(See, e.g., Ray et al., "Molecular Diagnostic Test for Ascertainment of Genotype at the Rod Cone Dysplasia (rcd1) Locus in Irish Setters," Current Eye Research, 14:243-247 (1995); Ray et al., "A Highly Polymorphic RFLP Marker in the Canine Transducin .alpha.-1 Subunit Gene," Animal Genetics, 27:372-373 (1996); Ray et al., "PCR/RFLP Marker in the Canine Opsin Gene," Animal Genetics, 27:293-294 (1996); Wang et al., "PCR/RFLP Marker in the Canine Transducin-.gamma. Gene (GNGT1)," Animal Genetics, 28:319-320 (1997); Gu et al., "Detection of Single Nucleotide Polymorphism," BioTechniques, 24:836-837 (1998) and Zeiss et al., "A Highly Polymorphic RFLP Marker in the Canine Retinitis Pigmentosa GTPase Regulator (RPGR) Gene," Animal Genetics, 29:409 (1998)). In addition to the rapidity of the PCR-RFLP technique, it also offers the flexibility to create an allele specific restriction site when the nucleotide change does not naturally create a RFLP. This is routinely done by deliberately incorporating a mismatch nucleotide in one of the primers such that a restriction site is created in one of the two alleles.

Nickerson et al. have described a nucleic acid detection assay that combines attributes of PCR and OLA (Nickerson et al., "Automated DNA Diagnostics Using an Elisa-Based Oligonucleotide Ligation Assay," Proc. Natl. Acad. Sci. USA, 87:8923-8927 (1990)). In this method, PCR is used to achieve the exponential amplification of target DNA, which is then detected using OLA.

Methods for Screening for Analogous Gene in Humans

Melanocytes are pigment-producing cells present in many tissues including the epidermis, hair follicle, inner ear, and choroid of the eye (Steingrimsson, E., et al., (2004) *Annu. Rev. Genet.* 38, 365-411). Melanocyte cell populations differentiate from unpigmented melanoblasts released from the neural crest during embryogenesis (Steingrimsson, E., et al., (2004) *Annu. Rev. Genet.* 38, 365-411). The complex process in which melanoblasts migrate and differentiate into melanocytes is not fully understood; however, the study of pigmentary anomalies has helped elucidate genes important for normal development (Mccallion, A. S., & Chakravarti, A. (2001) *Pigment Cell Res.* 14, 161-169).

Pigment cells play an important part in the hearing process, specifically in the process of translating the mechanical vibration that is a sound wave into the electrical impulse which can travel via nerves to the brain. The inner ear contains a tiny organ called a cochlea shaped like a snail's shell. It contains fluid and is lined with tiny hair-like structures called cillia. Sound vibrations travel through the ear canal and ultimately vibrates the fluid within the cochlea. Those vibrations wiggle the cilia, which are connected to nerve endings.

A pigment cell plays a key role in connecting each cilium to it's corresponding nerve. It "translates" the mechanical vibration into an electrical impulse. If the pigment cell is absent, this translation cannot take place. Therefore, fewer pigment cells (i.e., less pigment) results in greater hearing loss.

Waardenburg Syndrome (WS) is an autosomal dominant auditory-pigmentation disorder in humans (1 per 40,000 live births) that accounts for 2% of all cases of congenital deafness (Nayak and Isaacson 2003). Interfamilial and intrafamilial variability has been reported in WS type 1 and type 2, the most common forms of the syndrome (Choi, J. H., et al., (2004) *Korean J. Opthalmol.* 18, 185-189). Schaible and Brumbaugh (1976) were the first to suggest that phenotypic similarities exist between merling in dogs and WS in humans (Schaible, R. H., & Brumbaugh, J. A. (1976) *Pigment Cell* 3, 191-200). Classical features of both conditions are hypopigmentation of the hair, iris, and skin and sensorineural deafness. Four types of WS have been described based on clinical manifestations and mutations in five genes have been associated with the disorder: PAX3, MITF, SOX10, EDNRB, and EDN3 (Baldwin, C. T., et al., (1992) *Nature* 355, 637-638; Tassabehji, M., et al., (1992) Nature 355, 635-636; Pingault, V., et al., (1998) *Nat. Genet.* 18, 171-173; Puffenberger, E. G., et al., (1994) Cell 79, 1257-1266; Mccallion, A. S., & Chakravarti, A. (2001) *Pigment Cell Res.* 14, 161-169; Tassabehji, M., et al., (1994) *Nat. Genet.* 8, 251-255; and Choi, J. H., et al., (2004) *Korean J. Ophthalimol.* 18, 185-189).

The mutant phenotype of SILV in the human is unknown (Sturm, R. A., Teasdale, R. D., & Box, N. F. (2001) *Gene* 277, 49-62). Described herein is the first mutation in SILV that causes a disease process and data to suggest a possible involvement in human auditory-pigmentation disorders. The similarity of canine pigmentation and auditory disorder in patients with WS 2 allows identification of other candidate genes by characterization of the gene SILV. This is accomplished by comparing WS 2 affected patients to normal individuals and sequencing to identify any nonsense, missense, insertion, deletion, or splicing mutations.

These results demonstrate that the first mutation in a SILV causing a disorder has been identified and that SILV is important for normal development of multiple organs. Since dogs with merle are similar in phenotype in many respects to human with WS, dogs with merle are candidate model systems for study of WS. SILV should be considered as a candidate gene for WS. These results also demonstrate that genetic testing of SILV facilitates identification of animals with "cryptic" merle and harlequins with single or double merle. Analysis for mutations in SILV also facilitates identification of merle in animals in which merle is hard to see due to their coat color. Such coat colors include, but are not limited to, cream, dapple and light sable.

The present invention will be further understood by reference to the following non-limiting examples.

EXAMPLE 1

Screening for Merle Gene

Materials and Methods

Sample collection. DNA samples were obtained from previous studies conducted in the Canine Genetics Laboratory at Texas A&M University and through contributions from participating owners and breeders. Whole blood or buccal cells were collected from all dogs and genomic DNA was isolated using the Puregene DNA Isolation Kit (Gentra Systems, Minneapolis, Minn., USA).

Genotyping. Fluorescently labeled primers were synthesized and multiplex PCR was performed for MSS-2 markers as described in Clark et al. (2004). PCR products were resolved with an internal size standard (GeneScan 500 LIZ, PE Biosystems, Foster City, Calif., USA) using an ABI 3730xl DNA Analyzer (PE Biosystems). Genotypes were determined using Genemapper® Software v3.5 (PE Biosystems).

Linkage analysis. Analyses for LD were carried out for all genotyped MSS-2 markers using 41 Shetland sheepdogs. For each marker, the allele more often associated with the merle dogs was identified and all other alleles were combined into a second independent class. Fisher's exact probability test for 2×2 tables was used to evaluate allelic frequencies between the merle and nonmerle dogs. By convention, a P-value of <0.0001 provides evidence for LD.

For one marker with evidence of LD, an additional 20 Shetland sheepdogs were genotyped and the P-value was recalculated.

Sequencing. Primers were designed to capture the complete exon and partial flanking intronic sequence for the 11 exons of SILV using the Boxer 6× sequence and the human intron-exon boundaries reported in Bailin et al. (Bailin, T., Lee, S., & Spritz, R. A. (1996) *The Journal of Investigative Dermatology* 106, 24-27).

TABLE 1

Primers for the SILV gene

| Primer | Forward | Reverse |
|---|---|---|
| Exon 1 | GTAGCGGGATGTCCAGGG (SEQ ID NO: 2) | GAGAAAAATCAGAGCAGGTGTG (SEQ ID NO: 3) |
| Exons 2 and 3 | ATGGTGCTGTCCCCTGA (SEQ ID NO: 4) | ATCTGAGCCCTTGGAATAA (SEQ ID NO: 5) |
| Exon 4 | GGTTTGAGGGTGACTCTGTGT (SEQ ID NO: 6) | GGGCAGTGAAGATTTAGGGAA (SEQ ID NO: 7) |
| Exon 5 | TTCCCTATGCTCAGTTCTTCC (SEQ ID NO: 8) | GCTTTGCCCCTTCCCA (SEQ ID NO: 9) |
| Exon 6a | GGTGTGCCTGTGAAAGAAG (SEQ ID NO: 10) | CAAGCGTAGTGCCTGTGAC (SEQ ID NO: 11) |
| Exon 6b | GCAGATGACGACCACGG (SEQ ID NO: 12) | GTCCCACCTCAATGAACCT (SEQ ID NO: 13) |
| Exon 7 | GCCTCTTCAATCCTCTCC (SEQ ID NO: 14) | CAAGGTATGCTTTCACTGG (SEQ ID NO: 15) |
| Exon 8 | GAAGCAGCCTTACGGTTTT (SEQ ID NO: 16) | CGGAGTTCTCAGGACAATCA (SEQ ID NO: 17) |
| Exon 9 | CCATTGCCCTGACCTAAGC (SEQ ID NO: 18) | AGCCTGTCCAACGCCTG (SEQ ID NO: 19) |
| Exon 10 | TGGCGGGGAGCAGACA (SEQ ID NO: 20) | AAGAATGAGCAGTGGCAAGAG (SEQ ID NO: 21) |
| Exon 11 | CAGTTTCTCCTTTATTCTCCCA (SEQ ID NO: 22) | CCTCGGCAAATCACAGCA (SEQ ID NO: 23) |

Concentrations for an 8.45-μl PCR volume were 0.09 units/μl Taq DNA polymerase with 1.2× Buffer B (Fisher Scientific, Pittsburgh, Pa.), 3.55 mM $MgCl_2$, 1.2× MasterAmp PCR Enhancer (Epicentre Technologies, Madison, Wis.), 0.59 mM total dNTPs, 5.9 ng/μl DNA, 0.47 μM each forward and reverse primer, and 2.8 μl water. All exons were amplified with a single stepdown thermal cycling program: 5 min at 95° C. followed by 5 cycles of 30 sec at 95° C., 15 sec at 58° C., and 10 sec at 72° C., and an additional 30 cycles of 20 sec at 95° C., 15 sec at 56° C., and 10 sec at 72° C., with a final extension of 5 min at 72° C.

PCR products were analyzed by electrophoresis on a 3% agarose gel. The Qiagen XXX kit was used to purify amplicons. Products were ligated into pCR4.0-TOPO (Invitrogen, Carlsbad, Calif.) and transformed into chemically competent *Escherichia coli* TOP-10 cells (Invitrogen). Two clones for each dog were selected and sequenced. Sequences were aligned using Clustal W (WWW Service at the European Bioinformatics Institute).

Results

LD with the Merle Phenotype. Genotype data for 279 MSS-2 markers were generated for 9 merle and 32 nonmerle Shetland sheepdogs. Only one marker had an allele that appeared to be more common in the merle population. For this marker, FH2537, a statistically significant p-value ($7.2 \times 10^{-6}$) was obtained. To validate this result, additional genotype data were generated for the aforementioned marker using 7 merle, 2 double merle, and 11 nonmerle Shetland sheepdogs. These data were used to recalculate the p-value, which increased in significance ($9.0 \times 10^{-8}$).

Candidate Gene Selection. Focus was directed to genes implicated in the pigmentation system and proximal to FH2537, which is located in a region of CFA10 that exhibits conservation of synteny with HSA12q13. SILV, the human homolog to mouse silver, maps to HSA12q13-q14 (Kwon, B. S., et al., (1991) *Proc. Natl. Acad. Sci. USA* 88, 9228-9232) and encodes a melanosomal protein important in pigmentation (Sturm, R. A., Teasdale, R. D., & Box, N. F. (2001) *Gene* 277, 49-62). Furthermore, SILV expression is dependant upon MITF (Baxter and Pavan 2003), which has been implicated in WS type 2 and previously investigated as a candidate gene for merle (Tassabehji, M., Newton, V. E., & Read, A. P. (1994) *Nat. Genet.* 8, 251-255).

SINE Insertion. PCR was carried out using genomic DNA from two non-merle, one blue merle, and one double merle Shetland Sheepdog to obtain amplicons from each exon of SILV. Amplification of exon 11 yielded two products: the expected 206 bp product and a larger product (slightly smaller than 500 bp). These amplicons segregated with the merle phenotype among the aforementioned dogs: the non-merle dogs were homozygous for the 206 bp product, the blue merle was heterozygous for the products, and the double merle was homozygous for the larger product (FIGS. 1A, 1B and 1C).

Sequence analysis of exon 11 products revealed an insertion of a tRNA-derived SINE, highly similar to the unique canine SINEs first described by Minnick et al. ((Minnick, M. F., et al., (1992) Gene 110, 235-238)). The insertion occurs at the boundary of intron 10 and exon 11 (FIG. 2). DNA was available from 50 of the 61 Shetland Sheepdogs used in the linkage analysis. These 50 dogs were analyzed by gel electrophoresis for the insertion. The insert was present in the heterozygous state in 12 merles and in the homozygous state in 2 double merles. The insertion was also present in a non-merle that is suspected to be a cryptic because it was sired by a double merle; although no test breedings have been conducted to date to conclusively classified the dog as cryptic. Thirty-one non-merle dogs did not harbor the insertion and four non-merle dogs were heterozygous for a smaller insertion. Sequence analysis of this smaller insertion from two Shetland Sheepdogs revealed a deletion within the poly-A of the SINE.

EXAMPLE 2

Determination of Breed Specificity of Merle Gene

Figure 4:
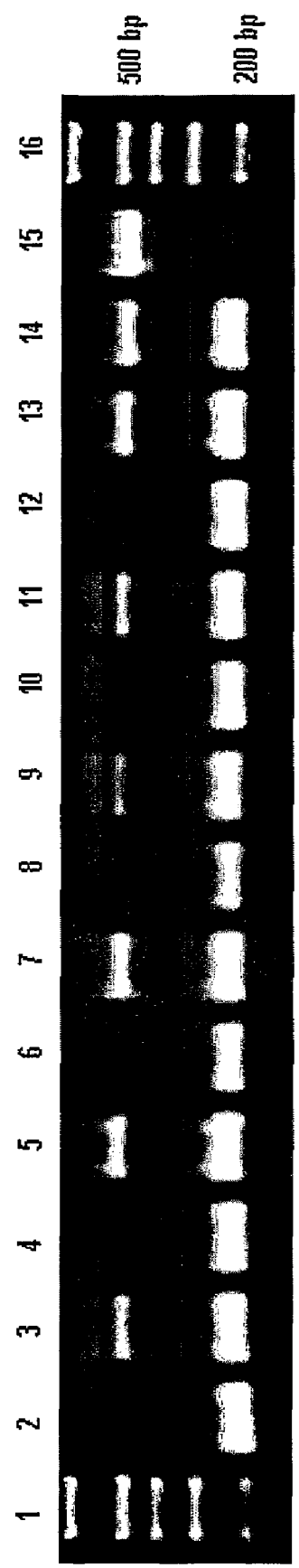
FIG. 4. Mutation analysis of SILV and its segregation in six breeds. PCR on genomic DNA from a sable/white Collie (lane 2), blue merle Collie (lane 3), black/white Border Collie (lane 4), blue merle Border Collie (lane 5), red Australian Shepherd (lane 6), blue merle Australian Shepherd (lane 7), brindle Cardigan Welsh Corgi (lane 8), blue merle Cardigan Welsh Corgi (lane 9), black/tan Dachshund (lane 10), red dapple Dachshund (lane 11), fawn Great Dane (lane 12), blue merle Great Dane (lane 13), and harlequin Great Danes (lane 14 and 15).

To determine if the SILV mutation causing merle patterning in the Shetland sheepdog population was breed specific, merle and nonmerle dogs representing six other breeds (collie, Australian shepherd, dachshund, Cardigan Welsh Corgi, border collie, and great dane) were analyzed for the insertion. Merle dogs from all other breeds were heterozygous for the insertion (FIG. 4).

Eleven harlequin great danes were also analyzed: 9 were heterozygous and 2 were homozygous for the insertion. Sequence analysis revealed that dogs from the aforementioned breeds harbored the same SINE insertion in intron 10. An additional 29 dogs representing 26 breeds that do not have merle coloration were analyzed and did not harbor the insertion.

Summary of Results

60 Shetland sheepdogs used in the linkage study were analyzed for the insertion, which segregated perfectly with the merle phenotype. The insertion also segregated with merle among dogs representing the collie, Australian shepherd, dachshund, Cardigan Welsh Corgi, border collie, and Great Dane breeds and sequence analysis confirmed that they harbor the same mutation. This finding suggests that the SINE insertion may have occurred as a founder event and that the seven breeds analyzed in this study share a common ancestor. Other breeds in which the merle phenotype has recently emerged include, but are not limited to, the Cocker spaniel, Pomeranian, and Chihuahua. The occurrence of merle in many breeds and the fact that the first breeds to diverge from the working sheepdog population in the 1800s have merle patterning (Collie, Old English Sheepdog, and Shetland Sheepdog), suggest that the founding mutation may predate the divergence of breeds (Neff, M. W., et al., (2004) Proc. Natl. Acad. Sci. USA 101, 11725-11730). Study of the history of the merle locus and phylogenetic analyses using subsequent mutations within the SINE insertion may help elucidate the evolutionary history of breeds (Shedlock, A. M. et al., (2004) Trends in Ecology and Evolution 19, 545-553).

Harlequin is a popular coloration in the Great Dane characterized by black patches on a white background. Studies of the inheritance of harlequin support the hypothesis that it is the result of two genes: a dominant gene (B) and the merle locus (M) (Sponenberg, D. P., & Bowling, A. T. (1985) J. Hered. 76, 393-394). A deficiency of white dogs (MM) from harlequin to harlequin matings has provided evidence to suggest that the H+ MM genotype has reduced viability (O'Sullivan, N., & Robinson, R. (1989) Genetica 78, 215-218). The identification of harlequin Great Danes homozygous for the SINE insertion in the present study suggest that harlequin dogs may be either H+ Mm or H+ MM. These data suggest that the H gene is dominant to M and that all white dogs have the ++MM genotype. This would account for the deficiency of white dogs observed in the aforementioned harlequin studies (Sponenberg, D. P., & Bowling, A. T. (1985) J. Hered. 76, 393-394 and O'Sullivan, N., & Robinson, R. (1989) Genetica 78, 215-218).

SILV in merle and normerle Shetland sheepdogs was characterized and a short interspersed repeat element (SINE) insertion at the intron 10/exon 11 boundary that segregates with the merle phenotype was identified. This insertion was found at the same site in six other breeds tested: collie, Australian shepherd, dachshund, border collie, Cardigan Welsh Corgi, and Great Dane and was consistent with merle patterning. The insertion was not present in dogs representing 26 breeds that do not have merle coloration. All harlequin Great Danes examined in this study harbored the insertion in either a heterozygous or homozygous state. One cryptic merle Shetland sheepdog examined was heterozygous for the insertion. An approximately 30 bp deletion within the SINE that permits normal pigmentation in dogs having the SINE insertion was also identified.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims. Those skilled in the art will recognize, or be able to ascertain using no more than routine experimentation, many equivalents to the specific embodiments of the invention described herein. Such equivalents are intended to be encompassed by the following claims.

We claim:

1. A method for identifying a merle and/or a cryptic merle allele in a canine animal, the method comprising:

analyzing a biological sample obtained from the canine animal for mutations in the SILV gene, wherein the presence of at least one insertion mutation at the boundary of intron 10 and exon 11 of the SILV gene indicates the canine animal has a merle or a cryptic merle allele, wherein the insertion comprises a short interspersed nucleotide element (SINE).

2. The method of claim 1, wherein the insertion is present between nucleotide positions corresponding to positions 43 and 44 of SEQ ID NO:24.

3. The method of claim 1, wherein the insertion is flanked by the first 15 nucleotides of any one of SEQ ID NOs:26-36.

4. The method of claim 1, wherein the merle allele is cryptic if the length of the poly-A segment of the SINE element is reduced by about 30 nucleotides relative to the length of any of the poly-A segments corresponding to the poly-T segments of the SINE elements shown in SEQ ID NOs:26-33.

5. The method of claim 1, wherein the canine animal is a dog.

6. The method of claim 1, wherein the canine animal has a merle allele.

7. The method of claim 6, wherein the merle allele comprises any one of SEQ ID NOs:26-33.

8. The method of claim 1, wherein the canine animal has a cryptic merle allele.

9. The method of claim 8, wherein the cryptic merle allele is SEQ ID NO: 34, 35 or 36.

10. The method of claim 1, wherein the biological sample is cell or tissue containing genomic DNA obtained from a dog.

11. The method of claim 1, wherein the biological sample is analyzed by performing PCR using genomic DNA as a template.

* * * * *

SEQUENCE LISTING

```
<160> NUMBER OF SEQ ID NOS: 36

<210> SEQ ID NO 1
<211> LENGTH: 1569
<212> TYPE: DNA
<213> ORGANISM: Canis familiaris

<400> SEQUENCE: 1
atggtacctt cgtttttagg acccagagac caggactggc ttggtgtccc aaggcagctc      60
```

```
acaactaaag cctggaacag acagctgtat ccagagtgga cagaaaccca gaggcctgac      120
tgctggagag gtgggaactt ggcaatttcc agggaggggtg gccaggtgtc cctgaaggtc    180
agtaatgatg ggcctacact ggttggtgca aatgcctcct tctctattgc cctgcacttc    240
cctgaaagcc aaaaggtact gccagatggg caggttgtct gggccaacaa cactatcatc    300
gatgggagcc aggtgtgggg aggacagcca gtgtatcccc aggtacttga tgatgcctgc    360
atcttccctg atgggagggc ctgcccatct ggcccttggt ctcagacaag aagctttgtt    420
tatgtctgga agacctgggt gtctgggctg agcattgtga caggcaaggc ggtgctgggc    480
acacatacca tggaagtgac tgtctaccac cgccgggagt cccagagcta cgtgcccctt    540
gctcactcct gctcagcctt caccattact gaccaggtgc ccttctccgt gagtgtgtct    600
cagctgcagg ccttggatgg agggaacaag catttcctga gaaatcatcc tctgaccttt    660
gccctccggc tccatgaccc cagcggctat ttgtctgggg ctgacctctc ctacacctgg    720
gactttggag accataccgg gaccctgatc tctcgggcac ttgtggtcac tcacacttac    780
ctagagtctg gcccaatcac tgcccaggtg gtcctgcagg ctgccattcc tctcacttcc    840
tgtggctcct ccccagttcc agtcaccaca gatgggcatg cgccaactgc agagatccct    900
ggcaccacag ctgggcgagt gcctactgca gaagtcataa agccctctgg aaccacaggc    960
gagcaggtaa cgactaaaga gtcagtggag cccacagctg gagagggacc cacgcctgag   1020
accaagggtc cagataccaa tctgttcgtg cctacagaag gtattacagg ttcccagagc   1080
gccctgctgg atggcacagc taccttaatc ctggcaaagc gagaaacccc cctggattgt   1140
gttctgtatc gatatggctc cttttctctc accctggaca ttgtccgggg tattgagaat   1200
gctgagatcc tgcaggctgt gccatccagt gaaggggatg catttgagct gactgtgtct   1260
tgccaaggcg gactgcccaa ggaagcctgc atggacatct catcaccagg gtgccagccc   1320
cctgcccaga ggctatgtca gcctgtgccg cccagcccag cctgccagct ggttttgcac   1380
caagtgctga agggtggctc agggacctac tgcctcaatg tgtctttggc tgatgctaac   1440
agtctggcaa tggtcagcac tcagcttgta atgcctggtc aagaagcagg cgttggacag   1500
gctcccctgt tcatgggcat cttgctggtg ttgctggcta tggtgctggt atctctgata   1560
tataggtga                                                            1569
```

<210> SEQ ID NO 2
<211> LENGTH: 18
<212> TYPE: DNA
<213> ORGANISM: Artificial Sequence
<220> FEATURE:
<223> OTHER INFORMATION: Forward Primer for Exon 1 of SILV gene

<400> SEQUENCE: 2

```
gtagcgggat gtccaggg                                                    18
```

<210> SEQ ID NO 3
<211> LENGTH: 22
<212> TYPE: DNA
<213> ORGANISM: Artificial Sequence
<220> FEATURE:
<223> OTHER INFORMATION: Reveerse Primer for Exon 1 of the SILV gene

<400> SEQUENCE: 3

```
gagaaaaatc agagcaggtg tg                                               22
```

<210> SEQ ID NO 4
<211> LENGTH: 17

```
<212> TYPE: DNA
<213> ORGANISM: Artificial Sequence
<220> FEATURE:
<223> OTHER INFORMATION: Forward primer for Exons 2 and 3 of the SILV
      gene

<400> SEQUENCE: 4
atggtgctgt cccctga                                                    17

<210> SEQ ID NO 5
<211> LENGTH: 19
<212> TYPE: DNA
<213> ORGANISM: Artificial Sequence
<220> FEATURE:
<223> OTHER INFORMATION: Reverse primer for Exons 2 and 3 of the SILV
      gene

<400> SEQUENCE: 5
atctgagccc ttggaataa                                                  19

<210> SEQ ID NO 6
<211> LENGTH: 21
<212> TYPE: DNA
<213> ORGANISM: Artificial Sequence
<220> FEATURE:
<223> OTHER INFORMATION: Forward primer for Exon 4 of the SILV gene

<400> SEQUENCE: 6
ggtttgaggg tgactctgtg t                                               21

<210> SEQ ID NO 7
<211> LENGTH: 21
<212> TYPE: DNA
<213> ORGANISM: Artificial Sequence
<220> FEATURE:
<223> OTHER INFORMATION: Reverse primer for Exon 4 of the SILV gene

<400> SEQUENCE: 7
gggcagtgaa gatttaggga a                                               21

<210> SEQ ID NO 8
<211> LENGTH: 21
<212> TYPE: DNA
<213> ORGANISM: Artificial Sequence
<220> FEATURE:
<223> OTHER INFORMATION: Forward primer for Exon 5 of the SILV gene

<400> SEQUENCE: 8
ttccctatgc tcagttcttc c                                               21

<210> SEQ ID NO 9
<211> LENGTH: 16
<212> TYPE: DNA
<213> ORGANISM: Artificial Sequence
<220> FEATURE:
<223> OTHER INFORMATION: Reverse primer for Exon 5 of the SILV gene

<400> SEQUENCE: 9
gctttgcccc ttccca                                                     16

<210> SEQ ID NO 10
<211> LENGTH: 19
<212> TYPE: DNA
<213> ORGANISM: Artificial Sequence
<220> FEATURE:
<223> OTHER INFORMATION: Forward primer for Exon 6a of the SILV gene
```

```
<400> SEQUENCE: 10
ggtgtgcctg tgaaagaag                                                    19

<210> SEQ ID NO 11
<211> LENGTH: 19
<212> TYPE: DNA
<213> ORGANISM: Artificial Sequence
<220> FEATURE:
<223> OTHER INFORMATION: Reverse primer for Exon 6a of the SILV gene

<400> SEQUENCE: 11
caagcgtagt gcctgtgac                                                    19

<210> SEQ ID NO 12
<211> LENGTH: 17
<212> TYPE: DNA
<213> ORGANISM: Artificial Sequence
<220> FEATURE:
<223> OTHER INFORMATION: FOrward primer for Exon 6b of the SILV gene

<400> SEQUENCE: 12
gcagatgacg accacgg                                                      17

<210> SEQ ID NO 13
<211> LENGTH: 19
<212> TYPE: DNA
<213> ORGANISM: Artificial Sequence
<220> FEATURE:
<223> OTHER INFORMATION: Reverse primer for Exon 6b of the SILV gene

<400> SEQUENCE: 13
gtcccacctc aatgaacct                                                    19

<210> SEQ ID NO 14
<211> LENGTH: 18
<212> TYPE: DNA
<213> ORGANISM: Artificial Sequence
<220> FEATURE:
<223> OTHER INFORMATION: FOrward primer for Exon 7 of the SILV gene

<400> SEQUENCE: 14
gcctcttcaa tcctctcc                                                     18

<210> SEQ ID NO 15
<211> LENGTH: 19
<212> TYPE: DNA
<213> ORGANISM: Artificial Sequence
<220> FEATURE:
<223> OTHER INFORMATION: Reverse primer for Exon 7 of the SILV gene

<400> SEQUENCE: 15
caaggtatgc tttcactgg                                                    19

<210> SEQ ID NO 16
<211> LENGTH: 19
<212> TYPE: DNA
<213> ORGANISM: Artificial Sequence
<220> FEATURE:
<223> OTHER INFORMATION: Forward primer for exon  8 of the SILV gene

<400> SEQUENCE: 16
gaagcagcct tacggtttt                                                    19

<210> SEQ ID NO 17
<211> LENGTH: 20
```

```
<212> TYPE: DNA
<213> ORGANISM: Artificial Sequence
<220> FEATURE:
<223> OTHER INFORMATION: Reverse primer for Exon 8 of the SILV gene

<400> SEQUENCE: 17
cggagttctc aggacaatca                                           20

<210> SEQ ID NO 18
<211> LENGTH: 19
<212> TYPE: DNA
<213> ORGANISM: Artificial Sequence
<220> FEATURE:
<223> OTHER INFORMATION: Forward primer for Exon 9 of the SILV gene

<400> SEQUENCE: 18
ccattgccct gacctaagc                                            19

<210> SEQ ID NO 19
<211> LENGTH: 17
<212> TYPE: DNA
<213> ORGANISM: Artificial Sequence
<220> FEATURE:
<223> OTHER INFORMATION: Reverse primer for Exon 9 of the SILV gene

<400> SEQUENCE: 19
agcctgtcca acgcctg                                              17

<210> SEQ ID NO 20
<211> LENGTH: 16
<212> TYPE: DNA
<213> ORGANISM: Artificial Sequence
<220> FEATURE:
<223> OTHER INFORMATION: Forward primer for Exon 10 of the SILV gene

<400> SEQUENCE: 20
tggcggggag cagaca                                               16

<210> SEQ ID NO 21
<211> LENGTH: 21
<212> TYPE: DNA
<213> ORGANISM: Artificial Sequence
<220> FEATURE:
<223> OTHER INFORMATION: Resverse primer for Exon 10 of the SILV gene

<400> SEQUENCE: 21
aagaatgagc agtggcaaga g                                         21

<210> SEQ ID NO 22
<211> LENGTH: 22
<212> TYPE: DNA
<213> ORGANISM: Artificial Sequence
<220> FEATURE:
<223> OTHER INFORMATION: Forward primer for Exon 11 of the SILV gene

<400> SEQUENCE: 22
cagtttctcc tttattctcc ca                                        22

<210> SEQ ID NO 23
<211> LENGTH: 18
<212> TYPE: DNA
<213> ORGANISM: Artificial Sequence
<220> FEATURE:
<223> OTHER INFORMATION: Reverse primer for Exon 11 of the SILV gene

<400> SEQUENCE: 23
```

```
cctcggcaaa tcacagca                                                 18

<210> SEQ ID NO 24
<211> LENGTH: 64
<212> TYPE: DNA
<213> ORGANISM: Canis familiaris

<400> SEQUENCE: 24
ccttgtccat tgctaatcga tttctccttt attctcccaa tgttaggcga agacttctga   60
agca                                                                64

<210> SEQ ID NO 25
<211> LENGTH: 79
<212> TYPE: DNA
<213> ORGANISM: Canis familiaris
<220> FEATURE:
<221> NAME/KEY: misc_feature
<222> LOCATION: (58)..(59)
<223> OTHER INFORMATION: SINE insertion

<400> SEQUENCE: 25
ccttgtccat tgctaatcag tttctccttt attctcccaa tgttagggga agacctctta   60
ggcgaagact tctgaagca                                                79

<210> SEQ ID NO 26
<211> LENGTH: 262
<212> TYPE: DNA
<213> ORGANISM: Canis familiaris

<400> SEQUENCE: 26
taggggaaga cctctttttt tttttttttt tttttttttt tttttttttt tttttttttt   60
tttttttttt tttttttttt ttttttttaa attttattt atttatgata gtcacagaga   120
gagagagagg cgcagagaca caggcagagg gagaagcagg ctccatgcac cgggagcccg   180
acgtgggatt cgatcccggg tctccaggat cgcgccctgg gccaaaggca ggcgccaaac   240
cgctgcgcca cccagggatc cc                                            262

<210> SEQ ID NO 27
<211> LENGTH: 266
<212> TYPE: DNA
<213> ORGANISM: Canis familiaris

<400> SEQUENCE: 27
taggggaaga cctctttttt tttttttttt tttttttttt tttttttttt tttttttttt   60
tttttttttt tttttttttt tttttttttt aaattttat ttatttatga tagtcacaga   120
gagagagaga gaggcgcaga gacacaggca gagggagaag caggctccat gcaccggag    180 cccgacgtgg gattcgatcc cgggtctcca ggatcgcgcc ctgggccaaa ggcaggcgcc   240
aaaccgctgc gccacccagg gatccc                                        266

<210> SEQ ID NO 28
<211> LENGTH: 274
<212> TYPE: DNA
<213> ORGANISM: Canis familiaris

<400> SEQUENCE: 28
taggggaaga cctctttttt tttttttttt tttttttttt tttttttttt tttttttttt   60
tttttttttt tttttttttt tttttttttt ttttttttaa attttatttt atttatgata   120
gtcacagaga gagagagaga ggcgcagaga cacaggcaga gggagaagca ggctccatgc   180
```

```
accgggagcc cgacgtggga ttcgatcccg ggtctccagg atcgcgccct gggccaaagg    240
caggcgccaa accgctgcgc cacccaggga tccc                                274

<210> SEQ ID NO 29
<211> LENGTH: 272
<212> TYPE: DNA
<213> ORGANISM: Canis familiaris

<400> SEQUENCE: 29 tagggggaaga cctctttttt tttttttttt tttttttttt tttttttttt              60
tttttttttt tttttttttt tttttttttt tttttaaat tttatttat ttatgatagt     120 cacagagaga gagagagagg cgcagagaca caggcagagg gagaagcagg ctccatgcac    180
cgggagcccg gcgtgggatt cgatcccggg tctccaggat cgcgccctgg gccaaaggca    240
ggcgccaaac cgctgcgcca cccagggatc cc                                 272

<210> SEQ ID NO 30
<211> LENGTH: 269
<212> TYPE: DNA
<213> ORGANISM: Canis familiaris

<400> SEQUENCE: 30
taggcgaaga cctcttttt tttttttttc tttttttttt tttttttttt tttttttttt     60
tttttttttt tttttttttt tttttttttt tttaaatttt tatttattta tgatagtcac   120
agagagagag agagaggcgc agagacacag gcagagggag aagcaggctc catgcaccgg   180
gagcccgacg tgggattcga tcccgggtct ccaggatcgc gccctgggcc aaaggcaggc    240
gccaaaccgc tgcgccaccc agggatccc                                      269

<210> SEQ ID NO 31
<211> LENGTH: 270
<212> TYPE: DNA
<213> ORGANISM: Canis familiaris

<400> SEQUENCE: 31
taggggaaga cctcttttt tttttttttt tttttttttt tttttttttt tttttttttt     60
tttttttttt tttttttttt tttttttttt ttttaaattt ttatttatt atgatagtca    120 cagagagaga gagagaggcg cagagacaca ggcagaggga gaagcaggct ccatgcaccg    180
ggagcccgac gtgggattcg atcccgggtc tccaggatcg cgccctgggc caaaggcagg    240
cgtcaaaccg ctgcgccacc cagggatccc                                     270

<210> SEQ ID NO 32
<211> LENGTH: 265
<212> TYPE: DNA
<213> ORGANISM: Canis familiaris

<400> SEQUENCE: 32 tagggggaaga cctctttttt tttttttttt tttttttttt ttctttttttt tttttttttt    60 tttttttttt tttttttttt tttttttttt taaatttta tttatttatg atagtcacag   120
agagagagag aggcgcagag acacaggcag agggagaagc aggctccatg caccgggagc    180
ccgacgtggg attcgatccc gggtctccag gatcgcgccc tgggccaaag gcaggcgcca    240
aaccgctgcg ccacccaggg atccc                                          265

<210> SEQ ID NO 33
```

-continued

```
<211> LENGTH: 268
<212> TYPE: DNA
<213> ORGANISM: Canis familiaris

<400> SEQUENCE: 33 tagggaaga cctcttttt tttttctt ttttttttt ttttttttt ttttttttt    60 tttttttt tttttttt tttttttt ttaaattt atttattt gatagtcaca       120 cagagagaga gagaggcgca gagacacagg cagagggaga agcaggctcc atgcaccggg    180
agcccgacgt gggattcgat cccgggtctc caggatcgcg ccctgggcca aaggcaggcg    240
ccaaaccgct gcgccaccca gggatccc                                      268

<210> SEQ ID NO 34
<211> LENGTH: 234
<212> TYPE: DNA
<213> ORGANISM: Canis familiaris

<400> SEQUENCE: 34
taggcgaaga cttcttttt tttttttt tttttttt tttttttt tttttttaa       60 atttttattt atttatgata gtcacagaga gagagagaga ggcgcagaga cacaggcaga    120
gggagaagca ggctccatgc accgggagcc cgacgtggga ttcgatcccg ggtctccagg    180
atcgcgccct gggccaaagg caggcgccaa accgctgcgc cacccaggga tccc          234

<210> SEQ ID NO 35
<211> LENGTH: 235
<212> TYPE: DNA
<213> ORGANISM: Canis familiaris

<400> SEQUENCE: 35
taggcgaaga cttcttttt tttttttt tttttttt tttttttt tttttttta       60 aattttatt tatttatgat agtcacagag agagagagag aggcgcagag acacaggcag    120
agggagaagc aggctccatg caccgggagc ccgacgtggg attcgatccc gggtctccag    180
gatcgcgccc tgggccaaag gcaggcgcca accgctgcg ccacccaggg atccc          235

<210> SEQ ID NO 36
<211> LENGTH: 227
<212> TYPE: DNA
<213> ORGANISM: Canis familiaris

<400> SEQUENCE: 36
taggcgaaga cttcttttt tttttttt tttttttt tttttttt taaatttta       60 tttatttatg atagtcacag agagagagag agaggcgcag agacacaggc agagggagaa    120
gcaggctcca tgcaccggga gcccgacgtg ggattcgatc ccgggtctcc aggatcgcgc    180
cctgggccaa aggcaggcgc caaaccgctg cgccacccag ggatccc                  227
```